US008880353B2

(12) United States Patent
Nakayama et al.

(10) Patent No.: US 8,880,353 B2
(45) Date of Patent: Nov. 4, 2014

(54) RIBONUCLEIC ACID IDENTIFICATION APPARATUS, RIBONUCLEIC ACID IDENTIFICATION METHOD, PROGRAM AND RIBONUCLEIC ACID IDENTIFICATION SYSTEM

(75) Inventors: Hiroshi Nakayama, Wako (JP); Misaki Akiyama, Wako (JP); Toshiaki Isobe, Tokyo (JP); Masato Taoka, Tokyo (JP); Yoshio Yamauchi, Tokyo (JP); Nobuhiro Takahashi, Tokyo (JP); Hideaki Ishikawa, Tokyo (JP)

(73) Assignees: Riken, Wako-shi (JP); Tokyo Metropolitan University, Tokyo (JP); National University Corporation Tokyo University of Agriculture and Technology, Tokyo (JP)

( * ) Notice: Subject to any disclaimer, the term of this patent is extended or adjusted under 35 U.S.C. 154(b) by 889 days.

(21) Appl. No.: 12/988,037

(22) PCT Filed: Apr. 17, 2009

(86) PCT No.: PCT/JP2009/057739
§ 371 (c)(1),
(2), (4) Date: Mar. 3, 2011

(87) PCT Pub. No.: WO2009/128526
PCT Pub. Date: Oct. 22, 2009

(65) Prior Publication Data
US 2011/0161273 A1    Jun. 30, 2011

(30) Foreign Application Priority Data

Apr. 17, 2008  (JP) .................................. 2008-108369

(51) Int. Cl.
*G01N 33/48* (2006.01)
*C12Q 1/68* (2006.01)
*H01J 49/00* (2006.01)

(52) U.S. Cl.
CPC ............... *C12Q 1/6872* (2013.01); *H01J 49/00* (2013.01)
USPC ........................................................ 702/19

(58) Field of Classification Search
None
See application file for complete search history.

(56) References Cited

FOREIGN PATENT DOCUMENTS

JP        2008-21260 A     1/2008
WO    WO 2008/007662 A1  1/2008

OTHER PUBLICATIONS

Toshiaki Isobe, "Taisha Chosetsu Kiko Kaiseki ni Motozuku Saibo Kino Seigyo Kiban Gijutsu", RNA Taisha Kaiseki no Tameno Shitsuryo Bunseki Pratform no Kaihatsu, JST Basic Research Programs Kenkyu Nenpo, 2007, vol. 2007, 5 pages.
Toshiaki Isobe, ""Taisha Chosetsu Kiko Kaiseki ni Motozuku Saibo Kino Seigyo Kiban Gijutsu", RNA Taisha Kaiseki no Tameno Shitsuryo Bunseki Pratform no Kaihatsu", JST Basic Research Programs Kenkyu Nenpo, 2006, Vo. 2006, 4 pages.
Jinsong Ni et al., Interpretation of Oligonucleotide Mass Spectra for Determination of Sequence using Electrospray Ionization and Tandem Mass Spectrometry, Analytical Chemistry, vol. 68, No. 13, Jul. 1, 1996, pp. 1989-1999.
Mary Grace Goll et al., Methylation OF tRNA$^{ASP}$ by the DNA Methyltransferase Homolog Dnmt2, Science, vo. 311, Jan. 20, 2006, pp. 395-398.
Mahmud Hossain et al., Mass Spectrometry-Based Detection of Transfer RNAs by Their Signature Endonuclease Digestion Products, RNA, vol. 13, Dec. 28, 2006, pp. 295-303.
David N. Perkins et al., Probability-Based Protein Identification by Searching Sequence Databases Using Mass Spectrometry Data, Electrophoresis, 20, 1999, pp. 3551-3567.
John R. Yates, III et al., Method to Correlate Tandem Mass Spectra of Modified Peptides to Amino Acid Sequences in the Protein Database, Analytical Chemistry, vol. 67, No. 8, Apr. 15, 1995, pp. 1426-1436.
Wenzhu Zhang et al., Profound: An Expert System for Protein Identification Using Mass Spectrometric Peptide Mapping Information, Analytical Chemistry, vol. 72, No. 11, Jun. 1, 2000, pp. 2482-2489.
Lewis Y. Geer et al., Open Mass Spectrometry Search Algorithm, Journal of Proteome Research, 3, 2004, pp. 958-964.
Rovshan G. Sadygov, Large-Scale Database Searching Using Tandem Mass Spectra: Looking Up the Answer in the Back of the Book, Nature Methods, vol. 1, No. 3, Dec. 2004, pp. 195-202.
Herbert Oberacher et al., Automated De Novo Sequencing of Nucleic Acids by Liquid Chromatography-Tandem Mass Spectrometry, American Society for Mass Spectrometry, 2004, 15, pp. 32-42.
Abstract of Siegel MM et al., An Efficient Algorithm for Sequencing Peptides Using Fast Atom Bombardment Mass Spectral Data, Biomed Environ Mass Spectrom., 15(6), Mar. 15, 1988, pp.

*Primary Examiner* — Eric S Dejong
(74) *Attorney, Agent, or Firm* — Foley & Lardner LLP

(57) ABSTRACT

Disclosed are an apparatus for the identification of a ribonucleic acid, whereby not only the molecular weights of digestion products, from which nothing but the nucleic acid residue composition can be understood, but also nucleic acid residue sequence data is obtained from a product ion mass set and thus the identification reliability for the individual digestion products can be remarkably improved; a method for the identification of a ribonucleic acid; and a program and system for the identification of a ribonucleic acid. The method as described above comprises: searching for nucleic acid sequence database by using a fragment mass set indicating the molecular weights and inner structural data of individual oligonucleotides that are obtained by tandem mass spectrometry on digested oligonucleotides formed by chemically or enzymatically cleaving a ribonucleic acid; scoring candidate sequences; among candidate sequences showing the highest scores, referring those showing scores exceeding the threshold as identified sequences; and using these identified sequences in mapping on nucleic acid sequence database including genomic sequences.

12 Claims, 23 Drawing Sheets

FIG. 1

| | OBJECT DATA | DB | MIXTURE | MODIFICATION | AMOUNT OF CALCULATION | OBJECT SAMPLE | | |
|---|---|---|---|---|---|---|---|---|
| | | | | | | PROTEIN | RNA | |
| mass fingerprinting | MW or mass | NEEDED | × | ○ | SMALL | NON-PATENT DOCUMENT 2 | PATENT DOCUMENT 1, NON-PATENT DOCUMENT 1 |
| MS/MS ion searching | MS/MS | NEEDED | ○ | ○ | MEDIUM | NON-PATENT DOCUMENTS 2 TO 6 | PRESENT INVENTION |
| denovo sequencing | MS/MS | NOT NEEDED | ○ | ○ | LARGE | NON-PATENT DOCUMENT 8 | NON-PATENT DOCUMENT 7 |

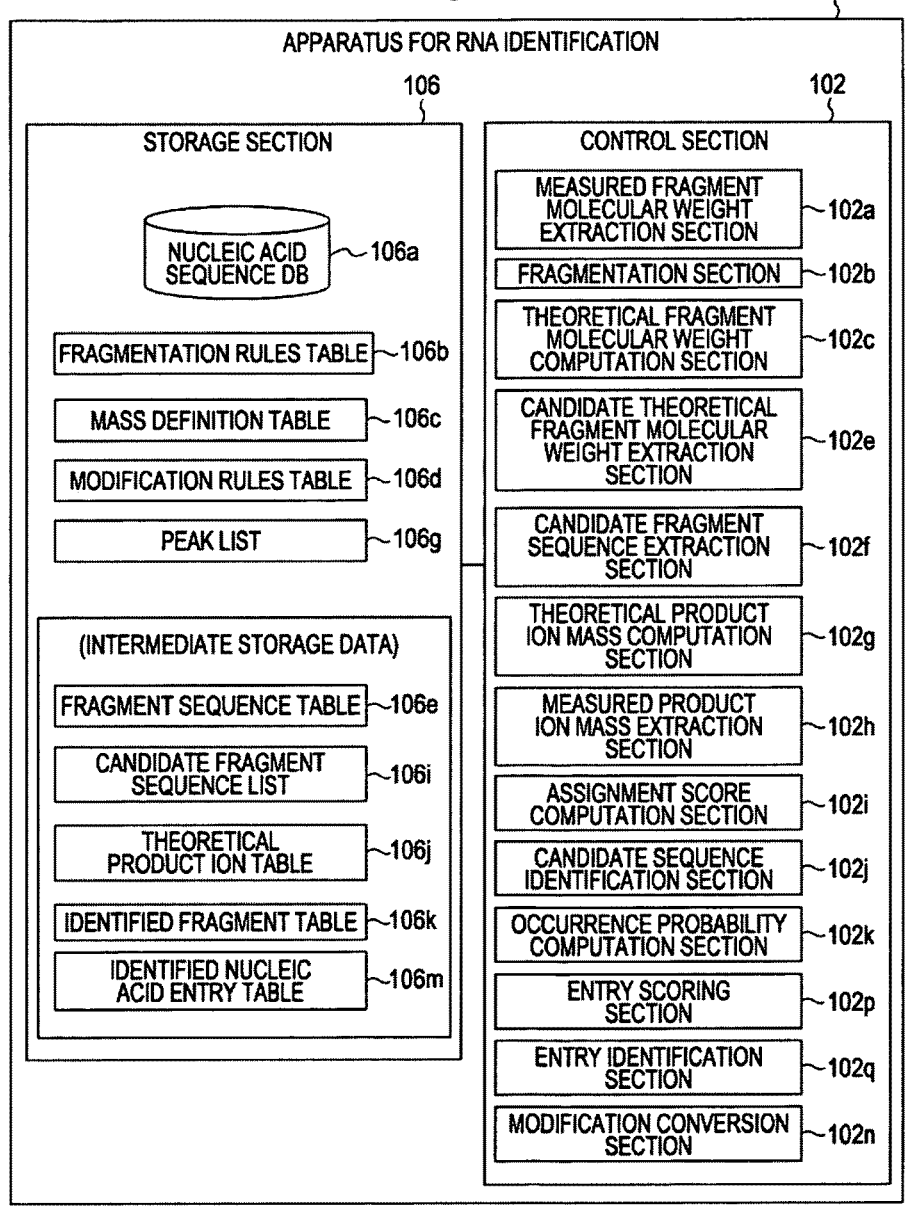

FIG. 11

| RNA_ID | mapping_score | number_of_match | number_of_digest | assignment |
|---|---|---|---|---|
| cypa | 187.1 | 43 | 75 | 3, 4, 5, 6, 10, 12, 14, 17, 18, 19, 20, 21, 22, 24, 25, 27, 29, 30, 32, 34, 35, 36, 37, 40, 42, 45, 46, 48, 49, 50, 51, 55, 56, 57, 58, 61, 64, 67, 69, 70, 71, 72, 74, 75, 76, 77, 80, 81, 82, 83. |
| FKBP | 160.3 | 34 | 49 | 3, 4, 5, 6, 10, 12, 13, 14, 15, 16, 17, 18, 19, 21, 22, 23, 25, 27, 28, 29, 30, 32, 33, 34, 36, 37, 38, 39, 41, 42, 43, 44, 46, 47, 48, 49, 52, 53, 54, 55. |

FIG. 13

| IDENTIFICATION (VISUAL INSPECTION) | IDENTIFICATION (SEARCH) | SITE | SEQUENCE | MODIFICATION | COMMENTS |
|---|---|---|---|---|---|
| – | – | 1–1 | G | NONE | |
| – | – | 2–3 | CG | NONE | |
| – | – | 4–4 | G | NONE | |
| ◎ | ◎ | 5–10 | AUUUAG | 10 m2G | 10 m2G WAS PARTIALLY DIGESTED |
| ◎ | ◎ | 5–15 | AUUUAGCUCAG | 10 m2G | |
| ○ | ○ | 11–15 | CUCAG | NONE | |
| ○ | ○ | 11–18 | CUCAGUUG | 16 D,17 D | |
| – | – | 16–18 | UUG | 16 D,17 D | |
| ◎ | ◎ | 19–19 | G | NONE | |
| – | – | 16–19 | UUGG | 16 D,17 D | |
| – | – | 20–20 | G | NONE | |
| – | – | 21–22 | AG | NONE | |
| – | – | 23–24 | AG | NONE | |
| – | – | 25–26 | CG | 26 m2G | m22G WAS NOT CLEAVED |
| – | – | 27–30 | CCAG | NONE | m22G WAS NOT CLEAVED |
| – | ◎ | 25–30 | CGCCAG | 26 m22G | MODIFICATION OTHER THAN OBJECT OF SEARCH, IDENTIFIED AS METHYLATION ON BOTH 25 AND 26 |
| – | – | 31–34 | ACUG | 32 Cm, 34 Gm | Gm WAS NOT CLEAVED |
| – | – | 35–37 | AAG | 37 yW | MODIFICATION OTHER THAN OBJECT OF SEARCH |
| – | – | 38–47 | AAAUACUUCG | ELIMINATED | NOT INCLUDED IN NATURE TYPE |
| – | – | 48–48 | G | ELIMINATED | NOT INCLUDED IN NATURE TYPE |
| – | – | 49–53 | UCAAG | ELIMINATED | NOT INCLUDED IN NATURE TYPE |
| – | – | 54–60 | UUAUCUG | 54-5ELIMINATED, 57 P, 58 m5C | |
| – | ◎ | 31–60 | ACUGAAGAUCUG | 32 Cm, 34 Gm, 37 yW, 57 P, 58 m5C | NATURE TYPE SEQUENCE, MODIFICATION OTHER THAN OBJECT OF SEARCH |
| – | – | 61–61 | G | NONE | |
| – | – | 62–63 | AG | NONE | |
| – | – | 64–64 | G | 64 m7G | m7G WAS NOT CLEAVED |
| – | – | 65–69 | UCCUG | 67 m6C | m7G WAS NOT CLEAVED |
| × | ◎ | 64–69 | GUCCUG | 64 m7G, 67 m6C | AN OBJECT OF SEARCH, BUT COULD NOT BE IDENTIFIED |
| – | – | 70–71 | UG | NONE | |
| ◎ | ◎ | 72–75 | UUCG | 73 T, 74 P | |
| ◎ | ◎ | 76–83 | AUCCACAG | 77 m1A | |
| ◎ | ◎ | 84–89 | AAUUCG | NONE | |
| ○ | ○ | 90–94 | CACCA | NONE | |

◎ A FRAGMENT HAVING 3 OR FEWER BASES, A FRAGMENT HAVING A MODIFICATION THAT IS NOT UNDER CONSIDERATION, OR A FRAGMENT THAT IS INCLUDED IN A DNA SEQUENCE ON A GENOME BUT IS NOT INCLUDED IN A NATURE TYPE tRNA BECAUSE THE FRAGMENT IS CLEAVED OUT DURING tRNA MODIFICATION
○ A FRAGMENT IDENTIFIED WHILE CONTAINING A MODIFICATION
○ A FRAGMENT IDENTIFIED WITHOUT A MODIFICATION
× A FRAGMENT THAT COULD NOT BE IDENTIFIED

FIG. 19

Query= gi|176405|gb|K01047.1|YSCRRA Saccharomyces cerevisiae 5S ribosomal RNA gene, complete sequence.
Length=121

>⌐ ref|NC_001144.4| ▣ Saccharomyces cerevisiae chromosome XII, complete chromosome sequence
Length=1078175
 Features in this part of subject sequence:
  rRNA-RDN5-1

Score = 213 bits (115), Expect = 7e-56
Identities = 120/122 (98%), Gaps = 2/122 (1%)
Strand=Plus/Plus

```
Query  1       GGTTGCGGCCATATCTACCAGAAAGCACCG-TTCTCCGTCCGATCAACTGTAGTTAAGCT  59
               ||||||||||||||||||||||||||||||| ||| ||||||||||||||||||||||||
Sbjct  459677  GGTTGCGGCCATATCTACCAGAAAGCACCGTTTC-CCGTCCGATCAACTGTAGTTAAGCT  459735

Query  60      GGTAAGAGCCTGACCGAGTAGTGTAGTGGGTGACCATACGCGAAACTCAGGTGCTGCAAT  119
               ||||||||||||||||||||||||||||||||||||||||||||||||||||||||||||
Sbjct  459736  GGTAAGAGCCTGACCGAGTAGTGTAGTGGGTGACCATACGCGAAACTCAGGTGCTGCAAT  459795

Query  120     CT  121
               ||
Sbjct  459796  CT  459797
```

Features in this part of subject sequence:
  rRNA-RDN5-6

Score = 213 bits (115), Expect = 7e-56
Identities = 120/122 (98%), Gaps = 2/122 (1%)
Strand=Plus/Plus Query  1       GGTTGCGGCCATATCTACCAGAAAGCACCG-TTCTCCGTCCGATCAACTGTAGTTAAGCT  59

FIG. 20

```
                   |||||||||||||||||||||||||||||| ||| ||||||||||||||||||||||||||
Sbjct  489350  GGTTGCGGCCATATCTACCAGAAAGCACCGTTTC-CCGTCCGATCAACTGTAGTTAAGCT  489408

Query  60      GGTAAGAGCCTGACCGAGTAGTGTAGTGGGTGACCATACGCGAAACTCAGGTGCTGCAAT  119
               ||||||||||||||||||||||||||||||||||||||||||||||||||||||||||||
Sbjct  489409  GGTAAGAGCCTGACCGAGTAGTGTAGTGGGTGACCATACGCGAAACTCAGGTGCTGCAAT  489468

Query  120     CT  121
               ||
Sbjct  489469  CT  489470
```

Features in this part of subject sequence:
  rRNA-RDN5-2
  Putative protein of unknown function identified by fungal...

Score = 206 bits (111),  Expect = 1e-53
Identities = 116/118 (98%), Gaps = 2/118 (1%)
Strand=Plus/Plus

```
Query  1       GGTTGCGGCCATATCTACCAGAAAGCACCG-TTCTCCGTCCGATCAACTGTAGTTAAGCT  59
               |||||||||||||||||||||||||||||| ||| ||||||||||||||||||||||||
Sbjct  468814  GGTTGCGGCCATATCTACCAGAAAGCACCGTTTC-CCGTCCGATCAACTGTAGTTAAGCT  468872

Query  60      GGTAAGAGCCTGACCGAGTAGTGTAGTGGGTGACCATACGCGAAACTCAGGTGCTGCA  117
               |||||||||||||||||||||||||||||||||||||||||||||||||||||||||
Sbjct  468873  GGTAAGAGCCTGACCGAGTAGTGTAGTGGGTGACCATACGCGAAACTCAGGTGCTGCA  468930
```

Features in this part of subject sequence:
  rRNA-RDN5-3
  Putative protein of unknown function identified by fungal...

Score = 206 bits (111),  Expect = 1e-53

FIG. 21

Identities = 116/118 (98%), Gaps = 2/118 (1%)
Strand=Plus/Plus

```
Query   1       GGTTGCGGCCATATCTACCAGAAAGCACCG-TTCTCCGTCCGATCAACTGTAGTTAAGCT  59
                ||||||||||||||||||||||||||||| ||| ||||||||||||||||||||||||||
Sbjct   472466  GGTTGCGGCCATATCTACCAGAAAGCACCGTTTC-CCGTCCGATCAACTGTAGTTAAGCT  472524

Query   60      GGTAAGAGCCTGACCGAGTAGTGTAGTGGGTGACCATACGCGAAACTCAGGTGCTGCA  117
                ||||||||||||||||||||||||||||||||||||||||||||||||||||||||||
Sbjct   472525  GGTAAGAGCCTGACCGAGTAGTGTAGTGGGTGACCATACGCGAAACTCAGGTGCTGCA  472582
```

Features in this part of subject sequence:
rRNA-RDN5-4
Putative protein of unknown function identified by fungal...

Score = 206 bits (111), Expect = 1e-53
Identities = 116/118 (98%), Gaps = 2/118 (1%)
Strand=Plus/Plus

```
Query   1       GGTTGCGGCCATATCTACCAGAAAGCACCG-TTCTCCGTCCGATCAACTGTAGTTAAGCT  59
                ||||||||||||||||||||||||||||| ||| ||||||||||||||||||||||||||
Sbjct   482046  GGTTGCGGCCATATCTACCAGAAAGCACCGTTTC-CCGTCCGATCAACTGTAGTTAAGCT  482104

Query   60      GGTAAGAGCCTGACCGAGTAGTGTAGTGGGTGACCATACGCGAAACTCAGGTGCTGCA  117
                ||||||||||||||||||||||||||||||||||||||||||||||||||||||||||
Sbjct   482105  GGTAAGAGCCTGACCGAGTAGTGTAGTGGGTGACCATACGCGAAACTCAGGTGCTGCA  482162
```

Features in this part of subject sequence:
rRNA-RDN5-5
Putative protein of unknown function identified by fungal...

Score = 206 bits (111), Expect = 1e-53

FIG. 22

```
Identities = 116/118 (98%), Gaps = 2/118 (1%)
Strand=Plus/Plus

Query   1       GGTTGCGGCCATATCTACCAGAAAGCACCG-TTCTCCGTCCGATCAACTGTAGTTAAGCT  59
                |||||||||||||||||||||||||||||| ||| |||||||||||||||||||||||||
Sbjct   485698  GGTTGCGGCCATATCTACCAGAAAGCACCGTTTC-CCGTCCGATCAACTGTAGTTAAGCT  485756

Query   60      GGTAAGAGCCTGACCGAGTAGTGTAGTGGGTGACCATACGCGAAACTCAGGTGCTGCA    117
                ||||||||||||||||||||||||||||||||||||||||||||||||||||||||||
Sbjct   485757  GGTAAGAGCCTGACCGAGTAGTGTAGTGGGTGACCATACGCGAAACTCAGGTGCTGCA    485814
```

RIBONUCLEIC ACID IDENTIFICATION APPARATUS, RIBONUCLEIC ACID IDENTIFICATION METHOD, PROGRAM AND RIBONUCLEIC ACID IDENTIFICATION SYSTEM

TECHNICAL FIELD

The present invention relates to an apparatus for the identification of a ribonucleic acid, a method for the identification of a ribonucleic acid, a program, and a system for the identification of a ribonucleic acid, and more particularly, to an apparatus for the identification of a ribonucleic acid, which retrieves a sequence database using the mass spectrometry data (particularly, mass values of product ions produced by collision-induced dissociation) of a ribonucleic acid (hereinafter, indicated also as RNA, which is an abbreviation of ribonucleic acid) and identifies an RNA, a method for the identification of a ribonucleic acid, a program, and a system for the identification of a ribonucleic acid.

BACKGROUND ART

Methods for the identification of proteins through mass spectrometry have been hitherto developed.

For example, large numbers of methods of using a molecular weight set (mass fingerprinting), methods for retrieving a sequence database using tandem mass spectrometry (MS/MS) data (MS/MS ion search), and methods for obtaining partial sequence information only from MS/MS spectrum information (de novo sequencing) have been developed, and some of them are available as commercially marketed programs (Non-Patent Documents 2 to 6 and 8).

Furthermore, in recent years, attention has been focused on the functions of RNAs that do not encode proteins (non-coding RNAs), and methods for the identification of a RNA through mass spectrometry have been developed.

For example, there has been reported a method of confirming the presence of a digestion product of a certain RNA from a relatively simple RNA mixture, using the signature mass characteristic to the digestion product (Non-Patent Document 1).

Furthermore, there have also been reports on, for example, de novo sequencing of nucleic acids (Non-Patent Document 7).

Furthermore, for example, an apparatus and a method for the identification of a RNA sequence on the genome using the RNA molecular weight (Patent Document 1) have been reported.

Here, in the mass spectrometry of a protein, the amino acid residues that constitute the protein can be divided into a peptide bond part and a side chain part. Among these, a part that undergoes mass change depending on the type or modification of the amino acid residues is the side chain part, and the peptide bond part usually does not undergo mass change.

On the contrary, in RNAs/DNAs, a constituent nucleotide residue is composed of three parts of a phosphorus residue, a ribose (or a deoxyribose), and a base, and from the viewpoint of the mode of modification, the chemical structure of the nucleotide residue is more complicated than that of a protein. Among these, mass change due to modification can occur in both the ribose and the base. Furthermore, by reflecting this structure, the dissociation patterns of MS/MS spectra tend to be susceptible to complication. Furthermore, even between nucleic acids, RNAs and DNAs have different dissociation patterns, so that in an identification method involving a mass spectrometry of RNA/DNA, score allotment is required in accordance with the respective dissociation pathways.

Therefore, the conventional methods for the identification of a protein through mass spectrometry (as described in Non-Patent Documents 2 to 6) are specialized in proteins, and therefore, the conventional methods cannot be applied to RNAs.

PRIOR ART DOCUMENT

Patent Document

Patent Document 1: JP-A-2008-21260

Non-Patent Document

Non-Patent Document 1: Hossain, M. and Limbach, P. "Mass spectrometry-based detection of transfer RNAs by their signature endonuclease digestion products." 2007, RNA, 13, 1-9.

Non-Patent Document 2: Perkins D N, Pappin D J, Creasy D M, Cottrell J S. "Probability-based protein identification by searching sequence database using mass spectrometry data." 1999, Electrophoresis, 20, 3551-3567.

Non-Patent Document 3: Yates J R, Eng J K, McCormack A L, Schieltz D. "Method to correlate tandem mass spectra of modified peptides to amino acid sequence in the protein database." 1995, Anal. Chem. 67, 1426-1436.

Non-Patent Document 4: Zhang, W. and Chait, B. "ProFound: An expert system for protein identification using mass spectrometric peptide mapping information." 2000, Anal. Chem. 72, 2482-2489.

Non-Patent Document 5: Geer L Y, et al. "Open Mass Spectrometry Search Algorithm." 2004, J. Proteome Res. 3, 958-964.

Non-Patent Document 6: Sadygov R G, Cociorva D, Yates J R. "Large-scale database searching using tandem mass spectra: looking up the answer in the back of the book." 2004, Nat. Methods. 1, 195-202.

Non-Patent Document 7: Oberacher H, Mayr B M, Huber C G. Automated de novo sequencing of nucleic acids by liquid chromatography-tandem mass spectrometry. J Am Soc Mass Spectrom. 2004 January; 15(1): 32-42.

Non-Patent Document 8: Siegel M M, Bauman N. An efficient algorithm for sequencing peptides using fast atom bombardment mass spectral data. Biomed Environ Mass Spectrom. 1988 Mar. 15; 15(6): 333-43.

DISCLOSURE OF THE INVENTION

Problems to be Solved by the Invention

However, the conventional methods for RNA identification by mass spectrometry have a problem that individual components in a mixture sample cannot be identified, the specificity or reliability of identification is low, and the site of post-transcriptional modification cannot be identified.

For example, the technology of Patent Document 1 is essentially unable to determine a single sequence when dealing with the molecular weight of a single digested oligonucleotide, and therefore, a database search is performed using plural molecular weight sets that are generated as a result of enzymatic digestion of a single RNA. For this reason, the technology cannot be effectively applied in the case where plural RNAs are present in mixture in a sample. Furthermore, there are occasions in which only several enzymatically digested fragments can be obtained from small molecules having more or less twenty bases, such as miRNA, and there is a possibility that molecules may not be identified when only such molecular weight information is available. Thus, there is a problem that the reliability of identification is low.

The technology of Non-Patent Document 1 is able to confirm the presence of RNA in a relatively simple RNA mixture under limited conditions in which the list of potential RNAs is only of a small size. Thus, the technology cannot be referred to as a general method for the identification of RNA.

Furthermore, the technology of Non-Patent Document 7 requires high computational ability as compared with the method of performing a database search. Non-Patent Document 7 does not mention about the analysis of post-transcriptional modification, but particularly in the case of considering post-transcriptional modification, which is frequently detected in non-coding RNAs, the required computational capabilities increases exponentially.

In recent years, as the progress of the genome sequencing technology is rapidly accelerating, there is a high possibility that the sequences that are objects of analysis may all be included in the database in the near future, and it is thought that from now on, the necessity of performing a spectral analysis without a database search will be gradually reduced, as described in this Non-Patent Document 7. FIG. 1 shows a summary of the ranking of methods for the identification of proteins and nucleic acids employing mass spectrometry data.

The present invention was made under such circumstances, and it is an object of the invention to provide an apparatus for the identification of a ribonucleic acid, a method for the identification of a ribonucleic acid, a program, and a system for the identification of a ribonucleic acid, which can significantly increase the identification reliability for individual digestion products by acquiring information on the nucleic acid residue sequence not only from the molecular weights of digestion products, which present only the composition of nucleic acid residues, but also from a set of product ion masses, which give information on the internal structures including sequences that are produced through MS/MS.

Means for Solving the Problems

In order to achieve the object of identifying a ribonucleic acid in the present invention, the apparatus for the identification of a ribonucleic acid of the present invention is an apparatus for the identification of a ribonucleic acid, including an information storage section and a control section, characterized in that the information storage section includes a peak data storage unit that stores the peaks of a spectrum extracted from tandem mass spectrometry data for a ribonucleic acid which has been cleaved by method of a base sequence-specific cleavage; a nucleic acid sequence storage unit that stores a nucleic acid sequence from each of nucleic acid entries; and a fragmentation rules storage unit that stores the fragmentation rules corresponding to the method of a base sequence-specific cleavage; and the control section includes a measured fragment molecular weight extraction unit that extracts measured fragment molecular weights from the peaks; a fragmentation unit that fragments the nucleic acid sequence by referring to the fragmentation rules; a theoretical fragment molecular weight computation unit that computes the theoretical fragment molecular weights for the fragment sequences of the nucleic acid sequence obtained as a result of the fragmentation executed at the fragmentation unit; a candidate theoretical fragment molecular weight extraction unit that extracts candidate theoretical fragment molecular weights corresponding to the measured fragment molecular weights by comparing the theoretical fragment molecular weights with the measured fragment molecular weights; a candidate fragment sequence extraction unit that extracts candidate fragment sequences, which are the fragment sequences corresponding to the candidate theoretical fragment molecular weights, from the fragment sequences; a theoretical product ion mass computation unit that computes the theoretical product ion masses for the fragment sequences according to predetermined dissociation rules; a measured product ion mass extraction unit that extracts measured product ion masses from the peaks; a score assigning unit that assigns a score to the candidate fragment sequences by comparing the theoretical product ion masses with the measured product ion masses; and a candidate sequence identification unit that identifies the fragment sequences of the ribonucleic acid from the candidate fragment sequences based on the scores.

The apparatus for the identification of a ribonucleic acid of the present invention is an apparatus for the identification of a ribonucleic acid as described above, characterized in that the control section further includes an occurrence probability computation unit that computes the occurrence probabilities for the fragment sequences of the nucleic acid sequence within a subset that has been previously designated as an object of search; an entry scoring unit that keeps mapping scores for the nucleic acid entries by comparing the nucleic acid sequence with the fragment sequences identified at the candidate sequence identification unit based on the occurrence probabilities; and an entry identification unit that identifies a most probable nucleic acid entry based on the mapping scores.

The apparatus for the identification of a ribonucleic acid of the present invention is an apparatus for the identification of a ribonucleic acid as described above, characterized in that the storage section further includes a modification rules storage unit that stores the rules for modification of the ribonucleic acid, and the control section further includes a modification conversion unit that performs conversion between a modified sequence and an unmodified sequence for each of the fragment sequences by referring to the modification rules.

Furthermore, the method for the identification of a ribonucleic acid of the present invention is a method for the identification of a ribonucleic acid executed in an apparatus for the identification of a ribonucleic acid including a control section and a storage section, the storage section including a peak data storage unit that stores the peaks of a spectrum extracted from tandem mass spectrometry data for a ribonucleic acid which has been cleaved by a residue-sequence-specific-cleavage method; a nucleic acid sequence storage unit that stores a nucleic acid sequence for each of nucleic acid entries; and a fragmentation rules storage unit that stores the fragmentation rules which are equivalent to the residue-sequence-specific-cleavage method, the method including the following steps which are executed at the control section: a measured fragment molecular weight extraction step of extracting measured fragment molecular weights from the peaks; a fragmentation step of fragmentizing the nucleic acid sequence by referring to the fragmentation rules; a theoretical fragment molecular weight computation step of computing theoretical fragment molecular weights for the fragment sequences of the nucleic acid sequence obtained as a result of the fragmentation executed in the fragmentation step; a candidate theoretical fragment molecular weight extraction step of extracting candidate theoretical fragment molecular weights that are corresponding to the measured fragment molecular weights by comparing the theoretical fragment molecular weights with the measured fragment molecular weights; a candidate fragment sequence extraction step of extracting candidate fragment sequences, which are fragment sequences corresponding to the candidate theoretical fragment molecular weights, from the fragment sequences; a theoretical product ion mass computation step of computing the theoretical product ion masses for the fragment sequences according to predetermined dissociation rules; a measured product ion mass extraction step of extracting measured product ion masses from the peaks; a scoring step of scoring the candidate fragment sequence by comparing the theoretical product ion masses with the measured product ion masses; and a candidate sequence identification step of identifying the fragment sequences of the ribonucleic acid from the candidate fragment sequences based on the scores.

The method for the identification of a ribonucleic acid of the present invention is a method for the identification of a ribonucleic acid as described above, characterized by further including the following steps which are executed at the control section: an occurrence probability computation step of computing the occurrence probabilities for the fragment sequences of the nucleic acid sequence within a subset that has been previously designated as an object of search; an entry scoring step of keeping mapping scores for the nucleic acid entries by comparing the nucleic acid sequence with the fragment sequence identified in the candidate sequence identification step based on the occurrence probabilities; and an entry identification step of identifying a nucleic acid entry that seems most probable based on the mapping scores.

The method for the identification of a ribonucleic acid of the present invention is a method for the identification of a ribonucleic acid as described above, characterized in that the storage section further includes a modification rules storage unit that stores the rules for modification of the ribonucleic acid, and the method further includes a modification conversion step, which is executed at the control section, of performing conversion between a modified sequence and an unmodified sequence for each of the fragment sequences by referring to the modification rules.

The program of the present invention is a program intended to be executed by an apparatus for the identification of a ribonucleic acid including a control section and a storage section, the storage section including a peak data storage unit that stores the peaks of a spectrum extracted from tandem mass spectrometry data for a ribonucleic acid which has been cleaved by a residue-sequence-specific-cleavage method; a nucleic acid sequence storage unit that stores a nucleic acid sequences for each of nucleic acid entries; and a fragmentation rules storage unit that stores the fragmentation rules which are equivalent to the residue-sequence-specific-cleavage method, the program including the following steps which are executed at the control section: a measured fragment molecular weight extraction step of extracting measured fragment molecular weights from the peaks; a fragmentation step of fragmentizing the nucleic acid sequence by referring to the fragmentation rules; a theoretical fragment molecular weight computation step of computing theoretical fragment molecular weights for the fragment sequences of the nucleic acid sequence obtained as a result of the fragmentation executed in the fragmentation step; a candidate theoretical fragment molecular weight extraction step of extracting candidate theoretical fragment molecular weights that are corresponding to the measured fragment molecular weights by comparing the theoretical fragment molecular weights with the measured fragment molecular weights; a candidate fragment sequence extraction step of extracting candidate fragment sequences, which are fragment sequences corresponding to the candidate theoretical fragment molecular weights, from the fragment sequences; a theoretical product ion mass computation step of computing theoretical product ion masses for the fragment sequences according to predetermined dissociation rules; a measured product ion mass extraction step of extracting measured product ion masses from the peaks; a scoring step of scoring the candidate fragment sequence by comparing the theoretical product ion masses with the measured product ion masses; and a candidate sequence identification step of identifying the fragment sequences of the ribonucleic acid from the candidate fragment sequences based on the scores.

The program of the present invention is a program as described above, characterized by further including the following steps which are intended to be executed at the control section: an occurrence probability computation step of computing the occurrence probabilities for the fragment sequences of the nucleic acid sequence within a subset that has been previously designated as an object of search; an entry scoring step of keeping mapping scores for the nucleic acid entries by comparing the nucleic acid sequences with the fragment sequences identified in the candidate sequence identification step based on the occurrence probabilities; and an entry identification step of identifying a nucleic acid entry that seems most probable based on the mapping scores.

The program of the present invention is a program as described above, characterized in that the storage section further includes a modification rules storage unit that stores the rules for modification of the ribonucleic acid, and the program further includes a modification conversion step, which is intended to be executed at the control section, of performing conversion between a modified sequence and an unmodified sequence for each of the fragment sequences by referring to the modification rules.

The present invention also relates to a recording medium, which is characterized in that the program described above is recorded therein.

According to this recording medium, the program described above can be realized using a computer, by allowing the computer to read out and run the program recorded in the recording medium, and thereby effects that are similar to these various methods can be obtained.

As such, the apparatus for the identification of a ribonucleic acid, the method for the identification of a ribonucleic acid, the program, and the system for the identification of a ribonucleic acid of the present invention are characterized in that a nucleic acid sequence database is retrieved by using a set of product ion masses which present the respective molecular weights and internal structure information of fragments, while this set is obtained by MS/MS of the fragments produced by the RNA residue-sequence-specific-cleavage method; candidate sequences are scored; those sequences having scores that are more than the threshold value, among the candidate sequences which have acquired the highest scores, are designated as identified sequences; and the identified sequences thus obtained are used to execute mapping of the nucleic acid sequence database containing genomic sequences. Here, the term "RNA residue-sequence-specific-cleavage method" includes, for example, enzymatic cleavage methods involving nucleases, chemical cleavage methods (see Document "Peattie D A. Direct chemical method for sequencing RNA. Proc Natl Acad Sci USA, 1979, April; 76(4):1760-4"), and the like. In the present specification, if an "RNA" is treated as an information transmission medium to which the base sequence of a DNA has been transcribed, the "RNA" is defined (prescribed) by the base sequence, as in the case of DNA. When RNA containing a modification in a base or ribose portion is handled, substrate specificity of RNA fragmentation enzyme (ribonuclease) cannot be specified (expressed) by base sequences alone because substrate specificity is affected not only by the type of bases, but also by modifications such as methylation of a base portion and ribose portion and also synthetic RNA in which a functional group is introduced into each of base, ribose, and phosphate portions may be used for RNA drug development. Thus, when "RNA" is handled as organic molecules (thing) (when substrate specificity cannot be specified (expressed) by base sequences alone), "RNA" is herein defined (expressed) by organic molecules formed by polymerization of mononucleotide units and the mononucleotide unit is defined as a "residue". Phosphate may be contained in (attached to) either the 5' terminal or the 3' terminal of nucleoside. More specifically, mass calculation may be made to be consistent by interpreting that the residue of the 3' terminal is subject to a modification of phosphate in 3' terminal processing of polynucleotide or the residue of the 5' terminal is subject to a modification of phosphate in 5' terminal processing Effect of the Invention According to the present invention, (1) measured fragment molecular weights are extracted from the peaks of a spectrum; (2) a nucleic acid sequence is fragmented by referring to the fragmentation rules; (3) theoretical fragment molecular weights are computed for the fragment sequences of the nucleic acid sequence obtained as a result of the fragmentation; (4) candidate theoretical fragment molecular weights that are corresponding to the measured fragment molecular weights are extracted by comparing the theoretical fragment molecular weights with the measured fragment molecular weights; (5) candidate fragment sequences, which are fragment sequences corresponding to the candidate theoretical fragment molecular weights, are extracted from the fragment sequences; (6) theoretical product ion masses are computed for the fragment sequences according to predetermined dissociation rules; (7) measured product ion masses are extracted from the peaks; (8) the candidate fragment sequences are scored by comparing the theoretical product ion masses with the measured product ion masses; and (9) the fragment sequences of the ribonucleic acid are identified from the candidate fragment sequences based on the scores.

In this manner, there is obtained an effect in which the identification reliability for individual digestion products can be drastically increased by acquiring information on the nucleic acid residue sequence not only from the molecular weights of digestion products, which present only the composition of nucleic acid residues, but also from a set of product ion masses.

Furthermore, according to the present invention, the occurrence probabilities for the fragment sequences of the nucleic acid sequence within the nucleic acid sequence database to be retrieved (a subset that has been previously designated as the object of search) are computed; mapping scores are kept for the nucleic acid entries by comparing the nucleic acid sequence with the fragment sequences (identified fragment sequences) of the RNA based on the occurrence probabilities; and a nucleic acid entry that seems most probable, is identified based on the mapping scores.

In this manner, there is obtained an effect in which mapping of a set of identified sequences to the database can be quantitatively evaluated.

Furthermore, according to the present invention, conversion between a modified sequence and an unmodified sequence is performed for the fragment sequences by referring to the modification rules. Then, the presence of post-transcriptional modification in the RNA contained in a sample is detected, and also, the site of modification is determined, with respect to the sequence database which does not contain modifications.

In this manner, there is obtained an effect in which the present invention can be applied even to samples containing modifications.

Finally, the effects described above are obtained when the present invention is applied, and consequently, there is obtained an effect that the present invention can also be applied to RNA mixtures.

BRIEF DESCRIPTION OF THE DRAWINGS

FIG. 1 is a table summarizing the differences in the characteristics of various analysis techniques for mass spectrometry (mass fingerprinting, MS/MS ion searching, and de novo sequencing), or the presence or absence of conventional technologies in the case of using proteins and RNAs as object samples;

FIG. 2 is a block diagram showing an example of the configuration of the present apparatus for RNA identification to which the present invention is applied;

FIG. 11 is a diagram showing an example of a comparison of the results obtained by searching against a merged database;

FIG. 13 is a table showing the results obtained by performing a search on tRNA-Phe with respect to the DNA sequence;

FIG. 19 is a diagram showing an example of the sequence region identified by mapping;

FIG. 20 is a diagram showing an example of the sequence region identified by mapping;

FIG. 21 is a diagram showing an example of the sequence region identified by mapping;

FIG. 22 is a diagram showing an example of the sequence region identified by mapping.

BEST MODE(S) FOR CARRYING OUT THE INVENTION

I. Overview of the Invention

Figure 3:
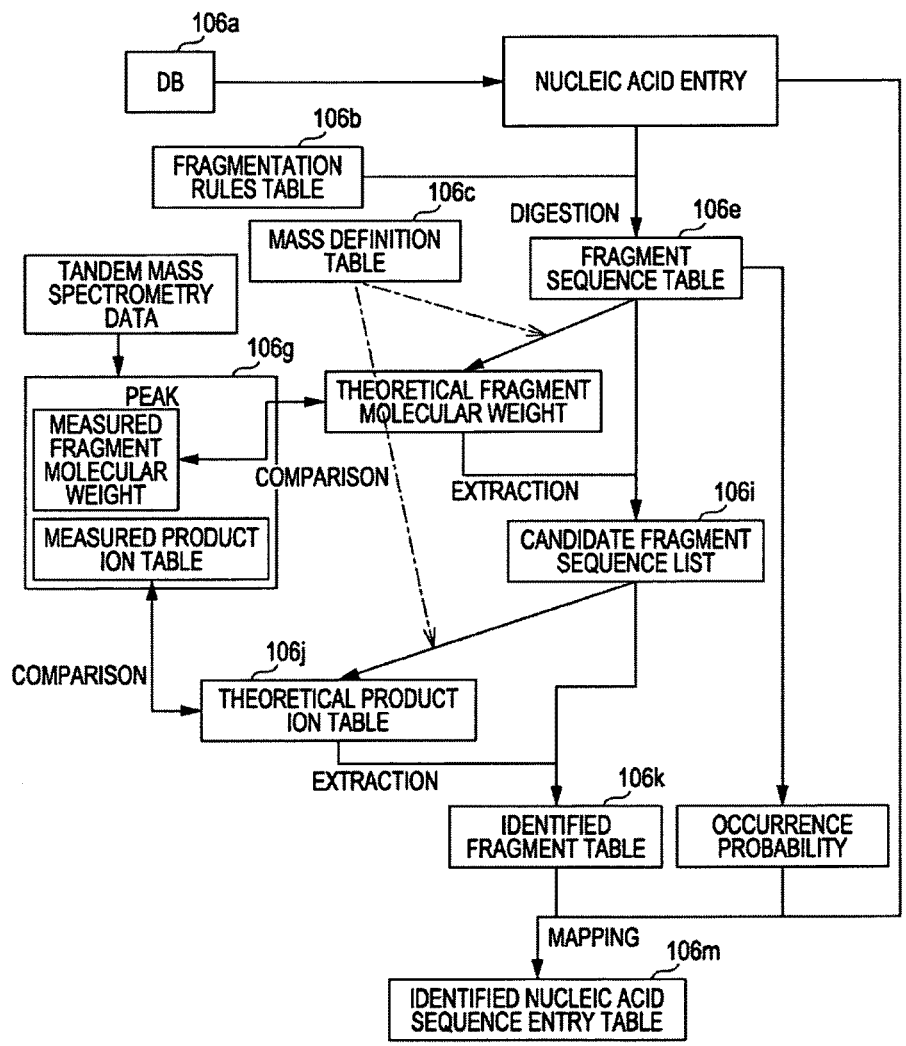
FIG. 3 is a flow diagram showing the data flow of RNA search made by the apparatus for RNA identification 100 according to the present exemplary embodiment.

The ranking of method for the identification of proteins and nucleic acids using mass spectrometry data is summarized in FIG. 1. The method for MS/MS ion searching of RNA is believed to be useful since the reliability of identification is higher compared with the mass fingerprinting method, and the amount of calculation is smaller than that of the de novo sequencing method. MS/MS ion searching is a general technique in the identification of proteins. However, in the case of applying this method to the identification of RNA, there are mainly posed three problems, and thus this method has not been hitherto applied.

(1) Since an RNA is composed of four types of nucleotide residues, the sequence diversity is small as compared with a protein, which is composed of 20 types of amino acid residues. For this reason, a single fragment sequence of about 10 residues in length may not allow identification of the original DNA/RNA. Particularly, in the case of retrieving a database for huge sequences such as genomes, it seldom occurs that a certain fragment sequence becomes unique in that database. Therefore, it is desirable that a method for RNA identification includes mapping as will be described below, due to that structural limitations.

(2) Post-transcriptional modification, which is frequently discovered in non-coding RNAs, is accompanied by diverse patterns of modification, as compared with proteins. That is, in the case of proteins, what can be usually modified is only the side chain of an amino acid residue. On the contrary to this, since modification of RNA can occur in any base or ribose, determination of the site of modification may be different. Furthermore, there are occasions in which a plural number of identical or different modifications may be achieved at plural sites of a single base. In an RNA molecule, modification such as methylation may occur in all of the four types of nucleosides. For this reason, search must be carried out while considering the possibility of modification for every residue. Furthermore, there are occasions in which plural sites of modification are present in a single residue, and there have also been reported many examples in which different functional groups are modifying at different sites. As such, in the MS/MS ion search of RNAs, it is necessary to handle modification forms which are not available in proteins.

(3) Conventionally, protein databases have been well organized, while databases concerning non-coding RNAs except for rRNA and tRNA are still undeveloped. With regard to non-coding RNAs, rules of from which site in a genome transcript are not yet established. Therefore, in the current situation, it is necessary to search both sides of the double strands of a genome or very long nucleic acid sequence, and thus the amount of calculation is enormous. Furthermore, it is also necessary to consider handling of the repeated regions of genomic DNAs.

In order to solve these problems, the present invention is constituted of the following two parts.

(1) MS/MS ion searching . . . . Fragment sequences are identified based on the molecular weight of the precursor ions of peaks obtained through tandem mass spectrometry of residue-specific fragmentation products, and on plural product ion masses.

(2) Mapping . . . . Mapping scores are kept for the entire nucleic acid entries by comparing the list of identified fragment sequences and the nucleic acid sequence in a database, and a nucleic acid entry that seems most probable is identified based on the relevant scores.

In the MS/MS ion searching of the present invention, identification reliability of fragments can be increased by a stochastic evaluation that will be described below. In the MS/MS ion searching of the present invention, search can be made while taking into consideration of the post-transcriptional modifications that are frequently found in non-coding RNAs, by deriving modified fragment sequences from the fragment sequences.

In the present invention, groups of fragment sequences that have been identified by MS/MS ion searching are mapped to various entries of the object of search database, and thereby the reliability of entry identification can be increased by a stochastic evaluation.

In the mapping of the present invention, the entries can be partitioned into sub-entries, so as to cope with huge database entries such as genomes. By partitioning the entries into sub-entries of an appropriate size, the location on the genome from which the RNA in the sample has been derived can be identified. Examples of the method of partitioning into sub-entries include a method based simply on the number of residues, a method based on the number of fragments, and a method based on the number of fragments excluding repetitions.

In the present invention, the target fragment sequence or entry is stochastically evaluated by the MS/MS ion searching or the mapping, respectively. That is, the probability for coincidental identification of individual fragment sequences or entries is determined, and the certainty of identification is evaluated using that probability. As the probability is lower, the possibility of occurrence of coincidence decreases. Therefore, it is thought that the identification is meaningful. Practically, scores are kept higher for lower probabilities for the purpose of facilitating the use, and the scores are used in the evaluation. However, in general, it cannot be said that the highest score itself for a certain object of search is meaningful. Thus, in the present invention, the threshold value can be used in order to objectively determine the significance of an obtained score. With regard to the threshold value, any one or both of a threshold value that is determined depending on the size of the database, and a threshold value that is determined by the distribution of the scores can be used.

II. Configuration of Apparatus for Identification of Ribonucleic Acid

FIG. 2 is a block diagram showing an example of the configuration of an apparatus for the identification of a ribonucleic acid to which the present invention is applied.

The apparatus for RNA identification 100 is configured to include a storage section 106 and a control section 102, and these sections are connected to each other to be capable of communication through an arbitrary communication channel.

The storage section 106 is set up to execute the means for storing a database or a table (nucleic acid sequence DB 106a to identified nucleic acid entry table 106*m*). The storage section may be a persistent storage device such as a hard disk, or may be a temporary storage device such as an RAM. These storage devices may be shared by the control section. Furthermore, the storage section 106 may store intermediate storage data that have been processed by the control section 102 (106*e*, 106*i* to 106*m*). In the following, the respective constituent elements of the storage section 106 will be explained.

A nucleic acid sequence DB 106*a* is set up to execute the means for storing a nucleic acid sequence information, by which means it stores nucleic acid entries. Here, the "nucleic acid entry" is a unit of search for nucleic acid sequences used to perform the identification of sequences, and the sequences are stored according to entry names. The "entry name" is an identity number or the like given in correspondence to the nucleic acid sequence for each nucleic acid entry. Suitably, an identity number or the like may be granted, as the entry name, in the form of a nucleic acid sequence unit corresponding to a single RNA species as an object of identification. Furthermore, here, the nucleic acid sequence DB 106*a* may store the nucleic acid sequences divided into predetermined subsets (human genomic sequences, mouse genomic sequences, human non-coding RNAs, and the like). Here, according to the present invention, the subset means a subset of the nucleic acid sequence DB 106*a*. The subset may be characterized by the name of species, type or properties of the molecule, and the like. Examples of the subset include human refseq, and mammal tRNA.

A fragmentation rules table 106*b* is set up to execute the means for storing a fragmentation rules, by which means it stores the fragmentation rules corresponding to the residue-sequence-specific-cleavage method. For example, in the case where RNase T1 is appointed, the fragmentation rules table 106*b* prescribes the 3'-side of guanine (G) in the sequence as the site of fragmentation, while in the case where Colicin E5 is appointed, the fragmentation rules table 106*b* prescribes the 3'-side of guanine of guanine-uracil (GU) sequence as the site of fragmentation.

A mass definition table 106*c* is set up to execute the means for storing a mass information, by which means it prescribes the mass of a ribose, a phosphate, or each base, which are all constituent elements of RNA to compute the molecular weight of RNA from the sequence. For example, the mass definition table 106*c* stores the symbols representing the elements or functional groups that constitute an RNA, in correlation to the respective masses, such as in the case of ribose: 115.0395, or adenine (A): 134.0467.

A modification rules table 106*d* is set up to execute the means for storing a modification information, by which means it stores the functional groups capable of modifying each of the RNA constituent elements. Examples of the modification information include methylation for a base or a ribose, deamination of an adenine base, and reduction of uridine to dihydrouridine. Furthermore, this modification rules table 106*d* may store the mass shifts caused by modification according to each of the modification patterns.

A peak list 106*g* is set up to execute the means for storing a peak information, by which means it stores the peaks extracted from tandem mass spectrometry data.

The control section 102 has an internal memory for storing the programs prescribing various procedures, and data required by the programs, or has a unit for executing the means of recognizing the data stored in the storage section or the storage unit shared by the storage section, and performs various information processing by these programs and the like. The control section 102 includes a measured fragment molecular weight extraction section 102*a*, a fragmentation section 102*b*, a theoretical fragment molecular weight computation section 102*c*, a candidate theoretical fragment molecular weight extraction section 102*e*, a candidate fragment sequence extraction section 102*f*, a theoretical product ion mass computation section 102*g*, a measured product ion mass extraction section 102*h*, an assignment score computation section 102*i*, a candidate sequence identification section 102*j*, an occurrence probability computation section 102*k*, an entry scoring section 102*p*, an entry identification section 102*q*, and a modification conversion section 102*n*. The respective elements of the control section 102 are explained below.

The measured fragment molecular weight extraction section 102*a* is set up as a unit to execute the means for extracting a measured fragment molecular weight, by which means it extracts measured fragment molecular weights corresponding to precursor ions in connection with the peaks stored in the peak list 106*g*.

The fragmentation section 102*b* is set up as a unit to execute the means for a fragmentation, by which means it fragments the nucleic acid sequence obtained from the nucleic acid sequence DB 106*a* by referring to the fragmentation rules table 106*b*.

The theoretical fragment molecular weight computation section 102*c* is set up as a unit to execute the means for computing a theoretical fragment molecular weight, by which means it computes theoretical fragment molecular weights for the fragment sequences of the nucleic acid sequence obtained as a result of fragmentation executed at the fragmentation section 102*b*.

The candidate theoretical fragment molecular weight extraction section 102*e* is set up as a unit to execute the means for extracting a candidate theoretical fragment molecular weight, by which means it extracts candidate theoretical fragment molecular weights from the peaks stored in the peak list 106*g*, comparing the measured fragment molecular weights extracted by the measured fragment molecular weight extraction section 102*a*, with the theoretical fragment molecular weights computed by the theoretical fragment molecular weight computation section 102*c*.

The candidate fragment sequence extraction section 102*f* is set up as a unit to execute the means for extracting a candidate fragment sequence, by which means it extracts fragment sequences that are corresponding to the candidate theoretical fragment molecular weights extracted by the candidate theoretical fragment molecular weight extraction section 102*e* as candidate fragment sequences.

The theoretical product ion mass computation section 102*g* is set up as a unit to execute the means for computing a theoretical product ion mass, by which means it computes theoretical product ion masses for given fragment sequences according to predetermined dissociation rules.

Here, the theoretical product ion mass computation section 102*g* can compute theoretical product ion masses that are corresponding to the product ions, for the candidate fragment sequences of the candidate fragment sequence list 106*i*. Here, the theoretical product ion mass computation section 102*g* can compute the theoretical product ion masses by referring to the mass definition table 106*c*, or can compute the theoretical product ion masses based on the molecular weight of each constituent element (phosphate, ribose, or each base) of the fragment sequences used by the theoretical fragment molecular weight computation section 102*c* in the case of computing theoretical fragment molecular weights.

The measured product ion mass extraction section 102*h* is set up as a unit to execute the means for extracting a measured product ion mass, by which means it extracts measured product ion masses from the peak list 106g.

The assignment score computation section 102i is set up as a unit to execute the means for scoring, by which means it keeps assignment scores for the candidate fragment sequences, comparing the theoretical product ion masses computed by the theoretical product ion mass computation section 102g, with the measured product ion masses extracted by the measured product ion mass extraction section 102h.

The candidate sequence identification section 102j is set up as a unit to execute the means for identifying a candidate sequence, by which means it extracts identified fragment sequences from the candidate fragment sequences based on the assignment scores kept by the assignment score computation section 102i.

The occurrence probability computation section 102k is set up as a unit to execute the means for computing occurrence probability, by which means it computes the occurrence probabilities for the fragment sequences of the nucleic acid sequence within a subset that has been previously designated as an object of search among the nucleic acid sequence sets stored in the nucleic acid sequence DB 106a.

The entry scoring section 102p is set up as a unit to execute the means for scoring an entry, by which means it keeps mapping scores for the nucleic acid entries by comparing the identified fragment sequences of an identified fragment table 106k with the nucleic acid sequences stored in the nucleic acid sequence DB 106a based on the occurrence probabilities computed by the occurrence probability computation section 102k.

The entry identification section 102q is set up as a unit to execute the means for scoring an entry, by which means it identifies a nucleic acid entry that seems likely (for example, seems most probable) based on the mapping scores kept at the entry scoring section 102p.

The modification conversion section 102n is set up as a unit to execute the means for converting a modification, by which means it performs conversion between a modified sequence and an unmodified sequence for each of the fragment sequences by referring to the modification rules stored in the modification rules table 106d. Here, the modification conversion section 102n can add modification to a nucleic acid sequence having no modification, or can remove modification from a fragment sequence so as to make an identified fragment sequence containing modification, equivalent to the original sequences of the nucleic acid entries.

III. Treatment of Present Apparatus for RNA Identification 100

Next, an example of the treatment of the apparatus for RNA identification 100 according to the present exemplary embodiment having a constitution such as described above, will be described with reference to FIGS. 2 and 3. FIG. 3 is a flow diagram showing the data flow of RNA search made by the apparatus for RNA identification 100 according to the present exemplary embodiment.

The order of the treatment of the apparatus for RNA identification 100 that will be presented below is merely an example, and the treatment is not intended to be limited to this order of explanation. Particularly, in regard to the treatment of measurement part (treatment of measured fragment molecular weight extraction section 102a) and the treatment of calculation parts (treatments of the fragmentation section 102b to theoretical fragment molecular weight computation section 102c) just before the treatment of the candidate theoretical fragment molecular weight extraction section 102e, any one of the treatments may be executed first, or the treatments may be executed simultaneously in parallel. Similarly, in regard to the treatment of measurement parts (treatment of the measured product ion mass extraction section 102h) and the treatment of calculation parts (treatments of the fragmentation section 102b to theoretical product ion mass computation section 102g) just before the treatment of the assignment score computation section 102i, any one of the treatments may be executed first, or the treatments may be executed simultaneously in parallel. Moreover, the calculation results made by the respective treatments of the calculation parts (fragmentation section 102b, theoretical fragment molecular weight calculation section 102c, and theoretical product ion mass computation section 102g) may also be inserted into a database in advance and stored in the fragment sequence table 106e or theoretical product ion table 106j of the storage section 106. The computation of occurrence probabilities may be carried out at the fragmentation section 102b, or may be carried out at any time between after the fragmentation and just before the entry scoring section 102p.

The fragmentation section 102b of FIG. 2 acquires a nucleic acid sequence for each of the nucleic acid entries from the nucleic acid sequence DB 106a, and fragments the nucleic acid sequence into fragment sequences based on the fragmentation rules which are equivalent to the appointed method for cleavage stored in the fragmentation rules table 106b. Here, the fragmentation section 102b may temporarily store the fragmentation results in the fragment sequence table 106e. Furthermore, the fragmentation section 102b may execute fragmentation for the nucleic acid sequences of an appointed subset. Here, the modification conversion section 102n may also add modification to a fragment sequence having no modification by referring to the modification rules table 106d.

Furthermore, a portion of the computation of occurrence probabilities may be carried out here, or the occurrence probability computation section 102k may compute the occurrence probabilities of the fragment sequences within a subset of nucleic acid sequences that have been previously designated as an object of search, among the nucleic acid sequences stored in the nucleic acid sequence DB 106a (for example, human refseq, yeast tRNA database, and the like), and may store the fragment sequences and the occurrence probabilities in the fragment sequence table 106e such that a fragment sequence is in correlation to its occurrence probability.

The calculation fragment molecular weight computation section 102c computes theoretical fragment molecular weights for the fragment sequences fragmented by the fragmentation section 102b by referring to the mass definition table 106c, and correlates the theoretical fragment molecular weights to the fragment sequences. Here, the theoretical fragment molecular weight computation section 102c may store the fragment sequences and the theoretical fragment molecular weights in the fragment sequence table 106e such that a fragment sequence is in correlation to its occurrence probability.

Meanwhile, the search query is the peak list 106g extracted from the tandem mass spectrometry data of an RNA which has been cleaved by a predetermined method for cleavage. Peak extraction from tandem mass spectrometry data can be carried out using a software program provided by the manufacturer of the mass analyzer (Xcalibur by Thermo Fisher Scientific, Inc.; Masslynx by Waters Corp.; or the like (company name)), or a commercially available software program (Mascot Distiller by Matrix Science, Ltd.; and the like (company name)). A typical peak list stores the molecular weights of fragments in correlation to the masses and intensities of product ions, as shown below.

Fragment 1 molecular weight
Product ion 1 mass, product ion 1 intensity
Product ion 2 mass, product ion 2 intensity
Product ion 3 mass, product ion 3 intensity
. . .
Product ion M mass, product ion M intensity
Fragment 2 molecular weight
Product ion 1 mass, product ion 1 intensity
Product ion 2 mass, product ion 2 intensity
Product ion 3 mass, product ion 3 intensity
. . .
Product ion N mass, product ion N intensity The peak list may contain additional information such as the mass, charge and intensity of a fragment ion, elution time, scan number, and comments, in addition to the information described above. A single peak list may contain peaks corresponding to plural MS/MS spectra. In this case, a peak and another peak may be delimited by appropriate delimiters. In the example shown above, the peaks are delimited by a blank line. Here, the peak list may have divided files for each peak. Furthermore, plural peak list files may be regarded as a single peak list and used in a single round of database search.

The measured fragment molecular weight extraction section 102a extracts measured fragment molecular weights from the peak list 106g as shown in FIG. 3.

Furthermore, the candidate theoretical fragment molecular weight extraction section 102e extracts candidate theoretical fragment molecular weights by comparing the extracted measured fragment molecular weights with the theoretical fragment molecular weights.

The candidate fragment sequence extraction section 102f extracts fragment sequences corresponding to the candidate theoretical fragment molecular weights extracted by the candidate theoretical fragment molecular weight extraction section 102e from the fragment sequence table 106e as candidate fragment sequences. The candidate fragment sequence extraction section 102f may store the extracted candidate fragment sequences in the candidate fragment sequence list 106i.

The theoretical product ion mass computation section 102g computes theoretical product ion masses for the candidate fragment sequences according to predetermined dissociation rules, and produces a theoretical product ion table 106j that stores the fragment sequences that serve as candidates in correlation to the respective ion names ("a1", "w3", and the like) of the product ions that will be described later and to the theoretical product ion masses.

Here, the main chain of an RNA is composed of two elements such as phosphate and ribose, and also has a structure in which a base that serves as a side chain is bonded to the ribose. Due to this structure, the site of dissociation is present at two points (5'-side: ribose-3'O-↓-P-5'O-↓-ribose:3'-side (here, the arrow "↓" represents the site of dissociation)) even in a low energy state, unlike peptides. When dissociation occurs between 2'O—P, the product ions of the 5'-terminal side are called as a-series, while the product ions of the 3'-terminal side are called as w-series. Furthermore, when dissociation occurs between 5'O—C, the product ions of the 5'-terminal side are called as c-series, while the product ions of the 3'-terminal side are called as y-series. The a-series and c-series containing the 5'-terminal are counted from the 5'-side, for example, as a1, a2, a3, and the like. On the contrary to this, the w-series and y-series containing the 3'-terminal are counted from the 3'-side.

The measured product ion mass extraction section 102h extracts measured product ion masses from the peak list 106g. For example, the measured product ion masses of peaks having ion intensities equal to or more than the threshold value, are extracted. Here, the measured product ion mass extraction section 102h may remove peaks that are corresponding to precursor ions from the measured product ion masses that are extracted based on the measured fragment molecular weights extracted by the measured fragment molecular weight extraction section 102a.

The assignment score computation section 102i keeps assignment scores for the candidate fragment sequences by comparing the theoretical product ion masses of the theoretical product ion table 106j computed by the theoretical product ion mass computation section 102g with the measured product ion masses extracted by the measured product ion mass extraction section 102h.

The candidate sequence identification section 102j identifies the fragment sequences of an RNA as identified fragment sequences, from the candidate fragment sequences of the candidate fragment sequence list 106i based on the assignment scores scored by the assignment score computation section 102i. Here, the candidate sequence identification section 102j may store the identified fragment sequences in correlation to the assignment scores, in the identified fragment table 106k. The occurrence probability computation section 102k computes the occurrence probabilities of the fragment sequences within a set of nucleic acid sequences (for example, human genomic sequences, and the like) that has been previously designated as an object of search among the nucleic acid sequences stored in the nucleic acid sequence DB 106a. The occurrence probability computation section 102k may also store the occurrence probabilities in correlation to the relevant fragment sequences in the identification fragment table 106k. Here, the fragment sequences of the fragment sequence table 106e, and the identified fragments of the identified fragment table 106k may be subjected to the respective treatments of modification conversion treatment, elimination of duplication, and derivation of missed cleavage(s) fragments.

The entry scoring section 102p keeps mapping scores for the nucleic acid entries by comparing the identified fragment sequences of the identified fragment table 106k with the nucleic acid sequences stored in the nucleic acid sequence DB 106a based on the occurrence probabilities of the identified fragment table 106k, and produces an identified nucleic acid entry table 106m. For example, the entry scoring section 102p evaluates those identified fragment sequences having higher occurrence probabilities, to have lower reliability for the RNA as an object of identification, and estimates lower mapping scores. Thereby, the identified nucleic acid entry table 106m stores the entry name, the mapping scores and the identified fragment sequence list according to the nucleic acid entry (plural identified fragment sequences derived from the nucleic acid sequence of the nucleic acid entry).

The entry identification section 102q identifies a nucleic acid entry that seems likely (for example, seems most probable) based on the mapping scores scored by the entry scoring section 102p. For example, the entry identification section 102q may determine the standard deviation for the plural mapping scores determined at the entry scoring section 102p, and may output those nucleic acid entries having a z-score which is equal to or more than the predetermined threshold value, as the identification results.

For the description above, the explanation of the overall treatment flow of the apparatus for RNA identification 100 is closed at this point. Next, more specific treatments for the treatments of the respective constituent elements of the apparatus for RNA identification 100 (measured fragment molecular weight extraction section 102a to modification conversion section 102n) described above will be explained below with reference to FIGS. 4 to 8.

[Treatment for Setting Search Conditions]

The apparatus for RNA identification 100 performs a search based on the search conditions including the following items (1) to (8). The apparatus for RNA identification 100 may be controlled to store search conditions in advance or to let the user specify the search conditions through an input apparatus.

(1) Species of organism: for example, human, yeast, mammals, all, and the like (2) Type of database: for example, genomic sequences, refseq, and the like (3) Method for cleavage: for example, nuclease names such as RNase T1, U2 and A, chemical cleavage method, and the like (4) Maximum number of missed cleavages to be considered: for example, about 0 to 3

(5) Maximum number of modifications to be considered: for example, about 0 to 3

(6) Mass tolerance: The mass accuracy of precursor ions and product ions may be different depending on the type of the tandem mass analyzer, for example, by about 10 to 500 ppm in accordance with the accuracy of the mass analyzer. In this case, different mass tolerance may be designated for different mass analyzers.

(7) Terminal functional group: for example, a phosphate group, a hydroxyl group, a cap (5' only),2',3'-cyclic phosphate (3' only), and the like (8) Mass table (stored in mass definition table 106c): table containing computed monoisotopic mass for each residue

[Fragmentation Treatment]

The nucleic acid sequences stored in the nucleic acid fragment DB 106a are DNA sequences or RNA sequences. A Fasta format file containing DNA sequences or RNA sequences may be designated as an object database (DB) for fragmentation.

When the nucleic acid sequences stored in the nucleic acid fragment DB 106a are RNA sequences, the fragmentation section 102b fragments a nucleic acid sequence obtained from the nucleic acid sequence DB 106a by referring to the selected fragmentation rules equivalent to the method for cleavage appointed by the user, which are stored in the fragmentation rules table 106b, as described above. However, when the nucleic acid sequences stored in the nucleic acid fragment DB 106a are DNA sequences, since the nucleic acid sequences themselves are not equivalent to the RNA sequences that are present in the living body, it is necessary to perform a transcription treatment (T→U), which is a conversion from a DNA sequence to an RNA sequence, as shown below. Furthermore, when the nucleic acid sequences stored in the nucleic acid sequence DB 106a are genomic DNAs, it is necessary to generate the complementary strands while making an assumption that an RNA is produced from both chains of the double strand.

Figure 4:
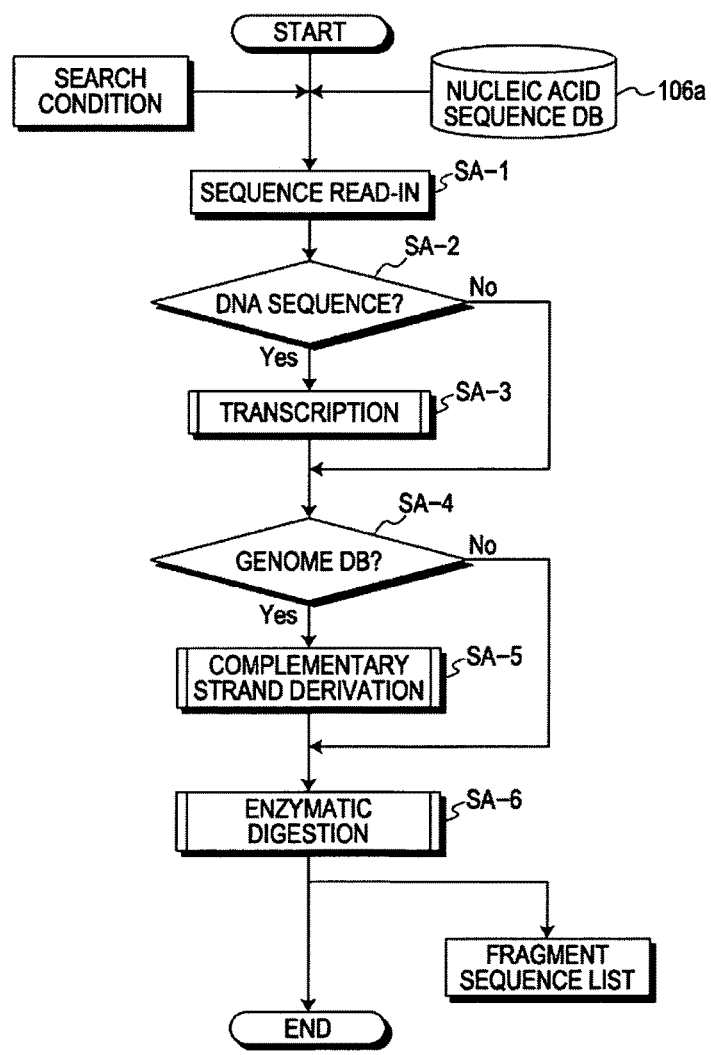
FIG. 4 is a flowchart showing an example of the database processing treatment according to the present exemplary embodiment.

As shown in FIG. 4, the fragmentation section 102b reads in a nucleic acid entry out of an appointed set of nucleic acid sequences from the nucleic acid sequence DB 106a based on the search conditions [Species of organism] and [Type of database] appointed by the user (step SA-1). Here, in the case where the nucleic acid sequence DB 106a is a genome DB or the like, and a single entry is huge, the fragmentation section 102b may partition this single nucleic acid entry into nucleic acid subentries. Examples of the method of partitioning into subentries include a method simply based on the number of residues, a method based on the number of fragments, and a method based on the number of fragments after unification of repetitive sequences.

The fragmentation section 102b then determines whether the read-in nucleic acid sequence is a DNA sequence (step SA-2).

If the fragmentation section 102b makes a determination that the nucleic acid sequence is a DNA sequence (step SA-2: Yes), the fragmentation section 102b performs a transcription treatment (step SA-3).

If the fragmentation section 102b makes a determination that the nucleic acid sequence is not a DNA sequence, that is, the sequence is an RNA sequence (step SA-2: No), or when the fragmentation section 102b has completed the transcription treatment (step SA-3), the fragmentation section 102b determines whether the nucleic acid sequence DB 106a, which is the source of read-in, is a genome DB (step SA-4).

If the fragmentation section 102b makes a determination that the nucleic acid sequence DB 106a is a genome DB (step SA-4: Yes), the fragmentation section 102b performs a complementary strand derivation treatment (step SA-5). Here, the complementary RNA strand derivation processing may be performed after the transcription processing as described or conversely, the transcription processing may be performed after derivation of complementary DNA.

Figure 5:
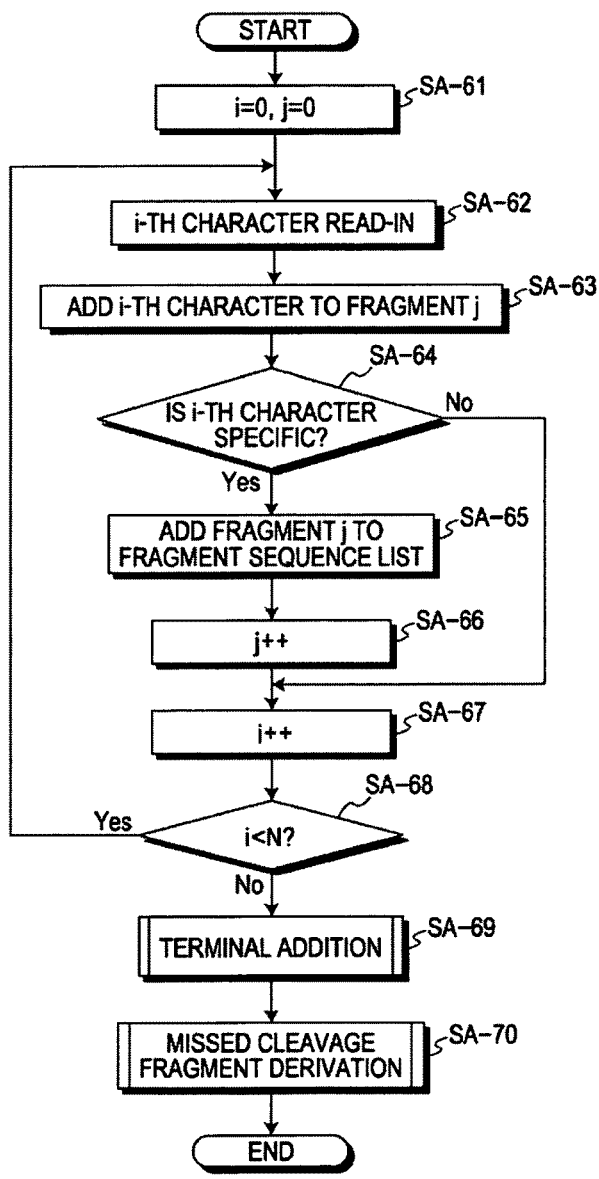
FIG. 5 is a flowchart showing an example of the enzymatic digestion treatment according to the present exemplary embodiment.

When the fragmentation section 102b makes a determination that the nucleic acid sequence DB 106a as the read-in source is not a genome DB (step SA-4: No), or when the fragmentation section 102b has completed the complementary strand derivation treatment (step SA-5), the fragmentation section 102b performs the residue sequence-specific fragmentation treatment shown below for the RNA sequence obtained by the treatments described above (step SA-6). Here, FIG. 5 shows a flowchart showing an example of the fragmentation treatment according to the present exemplary embodiment. In the following example, a case in which ribonuclease T1 (RNase T1), which is a single base-recognizing enzyme, is used as the residue sequence-specific cleavage method, will be explained. However, the present exemplary embodiment is not intended to be limited to the single base-recognizing enzyme, and an enzyme recognizing two or more bases may also be used. Furthermore, the method for cleavage is not intended to be limited to an enzymatic cleavage method, and use can also be made of a chemical cleavage method and the like.

(Enzymatic Digestion Treatment)

As shown in FIG. 5, first, the fragmentation section 102b sets a counter i and a fragment j to zero (step SA-61).

The fragmentation section 102b then reads in the sequence of the i-th character from the inputted RNA sequences (step SA-62).

The fragmentation section 102b then adds the i-th character to the fragment j (step SA-63).

The fragmentation section 102b then determines whether the i-th character is a specific residue sequence (step SA-64).

If the fragmentation section 102b makes a determination that the i-th character is a specific residue sequence (step SA-64: Yes), the fragmentation section 102b adds the fragment j to the fragment sequence list of the fragment sequence table 106e (step SA-65). On the other hand, if the fragmentation section 102b makes a determination that the i-th character is not a specific residue sequence (step SA-64: No), the fragmentation section 102b proceeds to the treatment of step SA-67.

The fragmentation section 102b performs an increment of one on the fragment j (j++) (step SA-66).

The fragmentation section 102b then performs an increment of one on the counter i (i++) (step SA-67).

The fragmentation section 102b then determines whether the read-in i-th character is smaller than the total number of characters N of RNA sequences (step SA-68).

If the read-in i-th character is smaller than the total number of characters N of RNA sequences (step SA-68: Yes), the fragmentation section 102b returns to the step SA-62 and repeats the treatment of the steps SA-62 to SA-68 described above.

If the read-in i-th character is equal to or more than the total number of characters N of sequences (step SA-68: No), the fragmentation section 102b adds a terminus to the fragment j according to the search condition [Terminal functional group] appointed by the user (step SA-69).

Furthermore, the fragment section 102b generates missed cleavage fragments according to the appointed search condition [Maximum missed cleavage to be considered] (step SA-70). For example, when the maximum missed cleavage is set to one spot, the fragmentation section 102b stores even those fragment sequences that are not fragmented at one spot among the specific residues searched by the treatment described above, in the fragment sequence table 106e.

Returning to FIG. 4 again, as described above, in the enzymatic digestive processing, the fragmentation section 102b continues the enzymatic digestion processing until all of the read-in sequences are fragmented, produces a fragment sequence list, and stores the fragment sequence list in the fragment sequence table 106e (step SA-6). In addition, when the sequences stored in the nucleic acid sequence DB 106a contains a symbol (for example, single-character indication N) for the case where the base could not be characterized, their molecular weights cannot be calculated, and thus the sequences may be excluded during the production of the fragment sequence list. Here, the modification conversion section 102n may add modifications to the fragment sequences having no modification by referring to the modification rules table 106d, according to the appointed search condition [Maximum number of modifications to be considered]. Furthermore, a part of the occurrence probability computation may be carried out herein, as will be described below.

[MS/MS Ion Searching Treatment]

Figure 6:
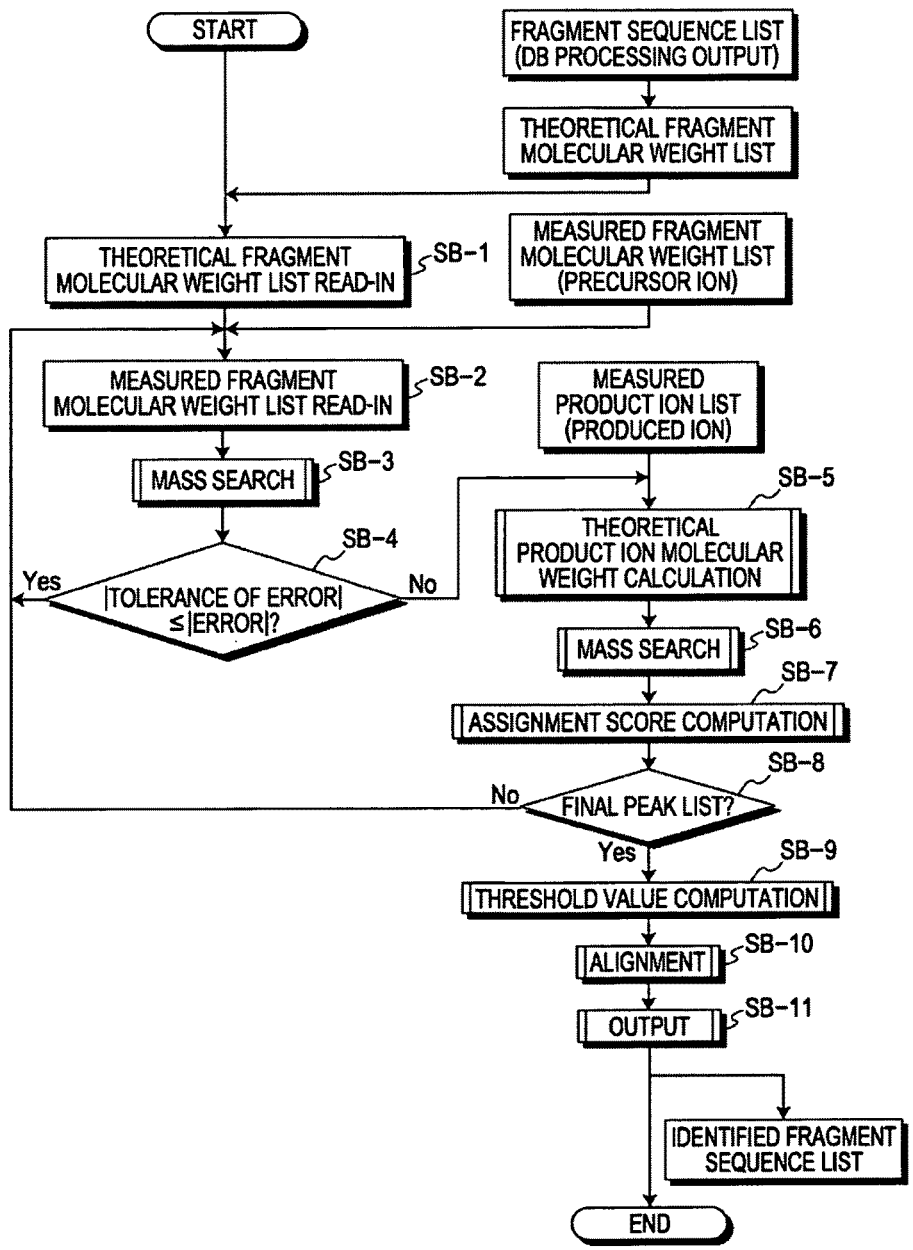
FIG. 6 is a flowchart showing an example of the MS/MS ion search treatment according to the present exemplary embodiment.

The apparatus for RNA identification 100 executes the following MS/MS ion searching treatment for the fragmented RNA sequences. The former process of the MS/MS ion searching treatment (steps SB-1 to SB-4) involves a mass search for precursor ions, which is executed by the measured fragment molecular weight extraction section 102a, theoretical fragment molecular weight computation section 102c, candidate theoretical fragment molecular weight extraction section 102e, and candidate fragment sequence extraction section 102f. On the other hand, the latter process of the MS/MS ion searching treatment (steps SB-5 to SB-11) involves a mass search for product ions. Here, FIG. 6 shows a flowchart showing an example of the MS/MS ion searching treatment according to the present exemplary embodiment.

First, the theoretical fragment molecular weight computation section 102c computes the theoretical fragment molecular weights corresponding to precursor ions for the respective fragment sequences of the fragment sequence list of the fragment sequence table 106e which has been produced by the fragmentation section 102b by referring to the mass definition table 106c, and produces a theoretical fragment molecular weight list. The apparatus for RNA identification 100 reads in the theoretical fragment molecular weight list (step SB-1).

The measured fragment molecular weight extraction section 102a reads in the measured fragment molecular weights corresponding to precursor ions, among the peak list 106g that stores the peaks extracted from the tandem mass spectrometry data by referring to the mass values (m/z) and charges (z) for the peaks of the MS1 spectrum (step SB-2).

The candidate theoretical fragment molecular weight extraction section 102e performs a mass search for the theoretical fragment molecular weight list in connection with the read-in measured fragment molecular weights (mass corresponding to the precursor ions) (step SB-3). Furthermore, when the search result is an empty set, the results are "missed."

The candidate theoretical fragment molecular weight extraction section 102e determines whether the theoretical fragment molecular weights of the search results are within a mass tolerance range of the search condition "Mass tolerance" appointed by the user (step SB-4).

If it is determined that the theoretical fragment molecular weights are not in the mass tolerance range (step SB-4: No), the candidate theoretical fragment molecular weight extraction section 102e returns to the step SB-2, reads in the measured product ion masses stored in the peak list 106g of another file, and repeats the treatments of the steps SB-2 to SB-4.

On the other hand, if it is determined that the theoretical fragment molecular weights are within the mass tolerance range (step SB-4: Yes), the candidate theoretical fragment molecular weight extraction section 102e designates the fragment sequences obtained from the fragment sequence table 106e, which is corresponding to the theoretical fragment molecular weights, as the candidate fragment sequences, produces a candidate fragment sequence list 106i, and proceeds to the next step SB-5.

The measured product ion mass extraction section 102h then extracts groups of measured product ion masses for the peaks of the MS2 spectrum stored in the peak list 106g. On the other hand, the theoretical product ion mass computation section 102g computes groups of theoretical product ion masses corresponding to various series of product ions, for each of the candidate fragment sequences of the candidate fragment sequence list 106i, according to predetermined dissociation rules, and produces a theoretical product ion table 106j (step SB-5).

The assignment score computation section 102i performs a mass search for the theoretical product ion table 106j in connection with the measured product ion masses (step SB-6).

The assignment score computation section 102i executes an assignment score computation treatment of keeping assignment scores for the candidate fragment sequences by comparing the theoretical product ion masses of the search results with the measured product ion masses (step SB-7).

The assignment score computation section 102i determines whether the peak list 106g obtained by performing the assignment score computation treatment is a final file of peak list (step SB-8).

If it is determined that the peak list 106g is not a final file of peak list (step SB-8: No), the assignment score computation section 102i returns to the treatment of the step SB-2, and repeats the treatment of the steps SB-2 to SB-8 described above for the peak list 106g of another file.

On the other hand, if the assignment score computation section 102i makes a determination that the peak list 106g is the final file of peak list (step SB-8: Yes), the candidate sequence identification section 102j computes the threshold value (step SB-9).

The candidate sequence identification section 102j identifies the fragment sequences of RNA from the candidate fragment sequences of the candidate fragment sequence list 106i as identified fragment sequences based on the assignment scores kept at the assignment score computation section 102i, and produces an identified fragment table 106k in which the fragment sequences are aligned (for example, sorted in a decreasing order) based on the assignment scores equal to or more than the computed threshold value (step SB-10). Here, when scoring for all of the fragments generated by dissociation in the candidate fragment sequences is completed, the candidate sequence identification section 102j compares each of the assignment scores with the threshold value. As a result of the comparison, if this score is higher than the threshold value, the candidate fragment sequence yielding this assignment score is designated as an identified fragment sequence. In addition, when a plural number of sequences yielding the maximum assignment scores are present, all of them may be regarded as identified fragment sequences.

Here, the data outputted based on the identified fragment table 106k may contain the group and property values (for example, molecular weight, assignment score, threshold value, MS2 assignment list, and the like) of the identified fragment sequences, and the like.

If the apparatus for RNA identification 100 does not continue performing the mapping treatment, the apparatus for RNA identification 100 outputs the results of fairing the identified fragment sequence set and the property values through the treatment of the candidate sequence identification section 102j based on the identified fragment table 106k. For the description above, the explanation of the example of the MS/MS ion searching treatment is closed at this point.

Now, the stochastic model employed by the apparatus for RNA identification of the present invention will be described below. When theoretical product ion masses contained in the theoretical product ion table 106j are present within the mass tolerance range set with respect to the measured product ion masses, these measured product ion masses are said to be matching.

According to the present exemplary embodiment, a simple stochastic model is used in which matching is assumed to be independent trials and the probability for each matching is constant, so as to decrease the amount of calculation. The present invention is not intended to be limited to this exemplary embodiment, and a stochastic model which does not execute matching independently (for example, matching of the y-series product ions are correlated with matching of the w-series product ions) and is not based on constant probabilities, may also be employed.

According to the stochastic model of the present exemplary embodiment, with regard to the MS/MS spectrum of a certain RNA fragment, when the number of peaks for which matching has been evaluated is designated as n, and the number of peaks that are hit among them is designated as x, the probability $P_{assign}$ by which these events occur simultaneously is as follows:

$$P_{assign} = {}_nC_m * p^x * (1-p)^{(n-x)}$$

Here, the term "$_nC_m$" is the number of cases of the combination of selecting m from n. This can be considered to be the same as the probability of having x times of same spots (for example, a spot of 1) when a dice is thrown n times.

The term "p" is the probability by which individual product ions coincidentally match. To compare this with dice rolling, the term corresponds to the question of how many sides does the dice have.

p is given by the formula: $p = M_{tol} * M_{center}/(M_{max} - M_{min})$ where, the term "$M_{tol}$" is the mass tolerance expressed in a relative value (for example, %, ppm, and the like); "$M_{center}$" is the center value of the measured mass range; and "$M_{max}$" and "$M_{min}$" are respectively the upper and lower limit values of the measured mass range.

The probability value $P_{assign}$ becomes very small in case of highly reliable results, which makes an intuitive mutual comparison difficult. Therefore, according to the present exemplary embodiment, $-\log P_{assign}$ is defined as 'assignment score'.

On the other hand, the threshold value for an evaluation of significant scores among the assignment scores computed by the assignment score computation section 102i, is determined, for example, in the following manner by the candidate sequence identification section 102j.

That is, the candidate sequence identification section 102j computes the "threshold value depending on the size of database" and/or "threshold value depending on the score distribution" in the manner shown below, as the threshold value of assignment scores according to the present exemplary embodiment.

Here, the "threshold depending on the database size" is a threshold obtained as an assign score when identification is accidentally generated with the significance level. More specifically, the probability that at least one of all candidates is accidentally identified, that is, the significance level p is given by $$p = 1 - (1-P)^N$$

where the probability that some candidate is accidentally identified is "P" (it is assumed that the probability of identifying any candidate is the same because the process is random), the number of candidate fragment sequences is "N".

When this is rearranged in terms of P, $$P = 1 - (1-p)^{1/N}$$

Here, 0.05 is normally used as the significance level, but different values such as 0.01 may also be used in accordance with the purpose of analysis or mass accuracy of a mass spectrometer.

Therefore, if identification of a fragment sequence can be achieved at a probability equal to or less than P, this identification can be said to be non-random.

That is, when the probability is expressed in a logarithmic value as in the case of the assignment score as described above, if the "$-\log P_{assign}$" which is the assignment score calculated by the assignment score computation section 102i, is larger than "$-\log P$" which is a threshold value computed by the candidate sequence identification section 102j, the identification can be evaluated as a significance. Then, the candidate sequence identification section 102j stores the corresponding candidate fragment sequence in the identification fragment table 106k as a candidate fragment sequence.

Here, the "threshold value dependent on the score distribution" may also be used as another method for evaluating identification. As the "threshold value depending on the score distribution," the use is made of, for example, an index representing how distant a certain assignment score is away from the distribution of assignment scores for a majority of fragment sequences that are incorrect. For example, when the score distribution can be regarded as a normal distribution, the z-score Z based on the following calculation formula may also be used.

$$Z = (s - S_{mean})/\sigma$$

Here, s represents the score of a certain fragment sequence; $S_{mean}$ mean represents an average value of the scores for all of the fragment sequences; and o represents the standard deviation of scores.

In addition, since the z-score as a threshold depends on the scoring method, the type of database, or the like, the threshold value may be specified in accordance with the experiment conditions.

[Mapping Treatment]

Next, the mapping treatment will be described in detail below with reference to FIGS. 7 and 8.

Here, in the mapping treatment, mapping may be carried out based on the type and number of fragment sequences included in the nucleic acid sequence. Furthermore, the occurrence probability of each fragment sequence is not limited to the computation by counting up, and an average occurrence probability for each length or another estimated occurrence probability may also be used.

The occurrence probability computation section 102k computes the occurrence probabilities of the fragment sequences in the set of nucleic acid sequences that has been previously appointed as an object of search among the nucleic acid sequences stored in the nucleic acid sequence DB 106a, and the entry scoring section 102p keeps mapping scores for the nucleic acid entries, based on the occurrence probabilities computed in the occurrence probability computation section 102k, by comparing the identified fragment sequences of the identified fragment table 106k with the nucleic acid sequences obtained from the nucleic acid sequence DB 106a. The entry identification section 102q identifies a nucleic acid entry that seems likely (for example, seem most probable) based on these mapping scores. Here, FIG. 7 is a flowchart showing an example of the mapping treatment according to the present exemplary embodiment.

Figure 7:
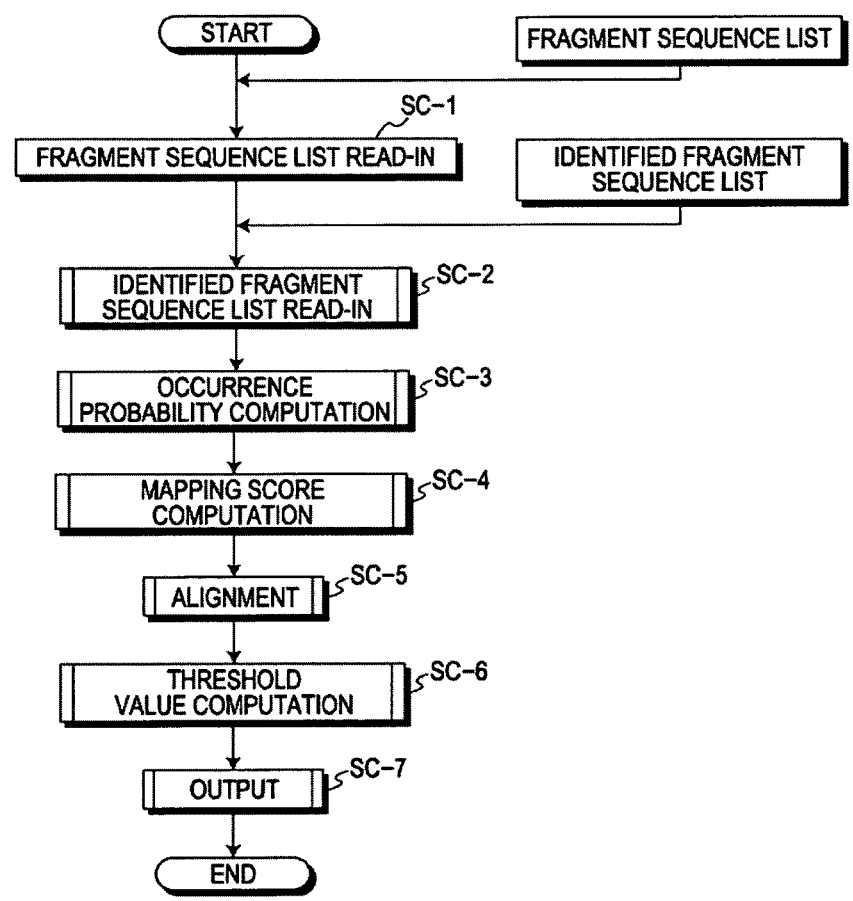
FIG. 7 is a flowchart showing an example of the mapping treatment according to the present exemplary embodiment.

As shown in FIG. 7, the entry scoring section 102p first reads in the fragment sequence list of the fragment sequence table 106e (step SC-1).

The entry scoring section 102p then reads in the identified fragment sequence list outputted by the candidate sequence identification section 102j (step SC-2).

Here, the fragment sequences of the fragment sequence table 106e and the identified fragments of the identified fragment table 106k may be subjected to the following treatment. That is, at the modification conversion section 102n, the nucleic acid sequences in the nucleic acid sequence DB 106a are DNA sequences and the like, and when these sequences have no modifications, any modifications may be removed from the identified fragment sequences to generate original sequences without modification. Furthermore, when duplication occurs in the list of identified fragment sequences with modifications, the modification conversion section 102n may remove the duplication. Furthermore, when duplication arises in an identified fragment sequence list obtained by removing modification, the modification conversion section 102n may remove such duplication. In addition, when the fragment sequences produced as a result of virtual fragmentation of each of the nucleic acid entries (or subentries) have duplication, the fragmentation section 102b may remove the duplication. The fragmentation section 102b may also store in advance the fragments from which missed cleavage fragments are generated according to the appointed search condition [Maximum number of missed cleavages to be considered] (when the maximum number of missed cleavages is appointed at one spot, even the fragment sequences that are not fragmented at one spot among the specific residues), in the fragment sequence table 106e.

The occurrence probability computation section 102k performs the following occurrence probability computation treatment (step SC-3). Here, FIG. 8 is a flowchart showing an example of the occurrence probability computation treatment according to the present exemplary embodiment.

Figure 8:
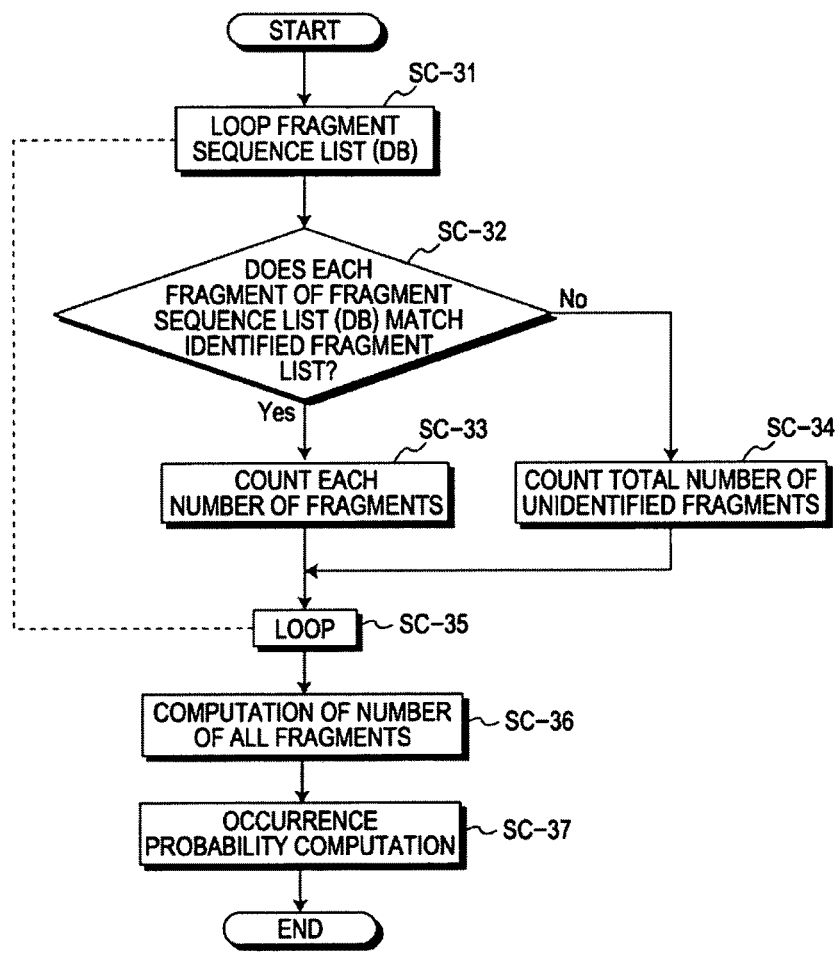
FIG. 8 is a flowchart showing an example of the occurrence probability computation treatment according to the present exemplary embodiment.

That is, as shown in FIG. 8, the occurrence probability computation section 102k determines, with regard to a fragment sequence list (DB) of the fragment sequence table 106e (step SC-31), whether the respective fragment sequences of the fragment sequence list (DB) match the identified fragment list of the identified fragment table 106k (step SC-32).

When the occurrence probability computation section 102k makes a determination that the fragment sequences match the identified fragment sequence list (step SC-32: Yes), the occurrence probability computation section 102k counts the number of matches for the respective fragments, for each of the fragments (step SC-33).

On the other hand, when the occurrence probability computation section 102k makes a determination that the fragment sequences do not match the identified fragment sequence list (step SC-32: No), the occurrence probability computation section 102k counts the total number of relevant fragment sequences as unidentified fragments (step SC-34).

The occurrence probability computation section 102k loops the treatments of step SC-31 to step SC-35 (step SC-35), and counts matches for all of the fragment sequences of the fragment sequence table 106e.

The occurrence probability computation section 102k then computes the number of all fragments of the fragment sequence table 106e (step SC-36).

The occurrence probability computation section 102k then computes the proportions of the respective numbers of identified fragment relative to the number of all fragments, as the occurrence probabilities of that identified fragment (step SC-37). Here, the proportion of the number of all unidentified fragments relative to the total number of fragments is defined as the occurrence probability of each of the unidentified fragments.

When processing of a portion of the occurrence probability computation section is carried out prior to the candidate sequence identification section, the sum of the occurrence probabilities of all of the unidentified fragments is determined here by referring to the identified fragment list, and this sum is designated as the occurrence probability of each of the unidentified fragments.

When plural fragment sequences from the precursor ions of one peak list are identified to have the same assignment scores at the candidate sequence identification section 102j of the [MS/MS ion searching treatment], these fragment sequences cannot be distinguished. Therefore, the sum of the occurrence probabilities of plural fragment sequences is computed, and this sum may be designated as the occurrence probability of each of the fragment sequences002E Returning to FIG. 7 again, the entry scoring section 102p performs the mapping score computation treatment of the nucleic acid entries (including subentries) (step SC-4).

In the computation of mapping scores, the mapping scores are computed while taking into consideration of the occurrence probabilities, by the correlation of the identified fragment sequences and the fragment sequences, and by counting those that matched and those that did not match, respectively. That is, according to the present exemplary embodiments, matching is regarded as an independent event, but the matching probabilities are not assumed to be constant, and the mapping scores are computed according to the occurrence probabilities of each fragment sequences in the actual database. In other words, according to the treatment of the entry scoring section 102$p$, under the assumption that individual fragment sequences appear randomly and independently, and the probability that a set of fragment sequences accidentally coexists in a nucleic acid sequence of some nucleic acid entry is computed. The entry scoring section 102$p$ then computes this selection probability by multiplying the respective occurrence probabilities of the fragment sequences generated from the nucleic acid entry (scoring may also be achieved by taking the –log values of the probabilities). As this probability of the accidental coexistence is small and its occurrence becomes rarer, it is considered that there is a high possibility that the relevant entry is contained in the original sample.

That is, the mapping scores according to the present exemplary embodiment are determined as follows.

The probability $P_{entry}$ that the entry is accidentally identified is given by $$P_{entry}=N!/(a!*b!*c!* \ldots n_{not}!)*p_A{}^a*p_B{}^b*p_C{}^c* \ldots p_{not}{}^{n_{not}}$$

where occurrence probabilities of matching fragments in a search target nucleic acid sequence database are $p_A$, $p_B$, $p_C$, ..., the sum of occurrence probabilities of fragments that do not match is $p_{not}$, the total number of fragments of some entry is N, numbers of matching fragments are a, b, c, ..., and the total number of non-matching fragments is $n_{not}$.

Here, in consideration of the weight of repetitive sequences, each fragment in the entry is considered as unique by removing duplication, the total number of fragments of some entry becomes equal to the number of types of fragments. In the case, $P_{entry}$ is given by the formula shown below:

$$P_{entry}=M!/(n_{not}!)*p_A*p_B*p_C* \ldots (p_{not})^{n_{not}}$$

where the total number is M.

The values obtained by taking the –log value of this selection probability $P_{entry}$ and scoring, may also be used as mapping scores.

Returning to FIG. 7 again, the entry identification section 102$q$ aligns (for example, sorting in a decreasing order) the nucleic acid entries based on the mapping scores kept at the entry scoring section 102$p$ (step SC-5).

The entry identification section 102$q$ then computes the threshold value of the mapping scores (step SC-6). Here, the entry scoring section 102$p$ may compute the threshold value depending on the size of the database. That is, the entry scoring section 102$p$ may compute the z-scores for the mapping scores of all nucleic acid entries, as described in the above.

The entry identification section 102$q$ excludes those nucleic acid entries having mapping scores that are equal to or lower than a predetermined threshold value (for example, threshold value appointed by the user as a search condition), and produces the identified nucleic acid entry table 106$m$. That is, in the entry identification section 102$q$, if a score is higher than the predetermined threshold value, the nucleic acid entry yielding this score is designated as an identified nucleic acid entry.

IV. Examples

Example 1

Figure 9:
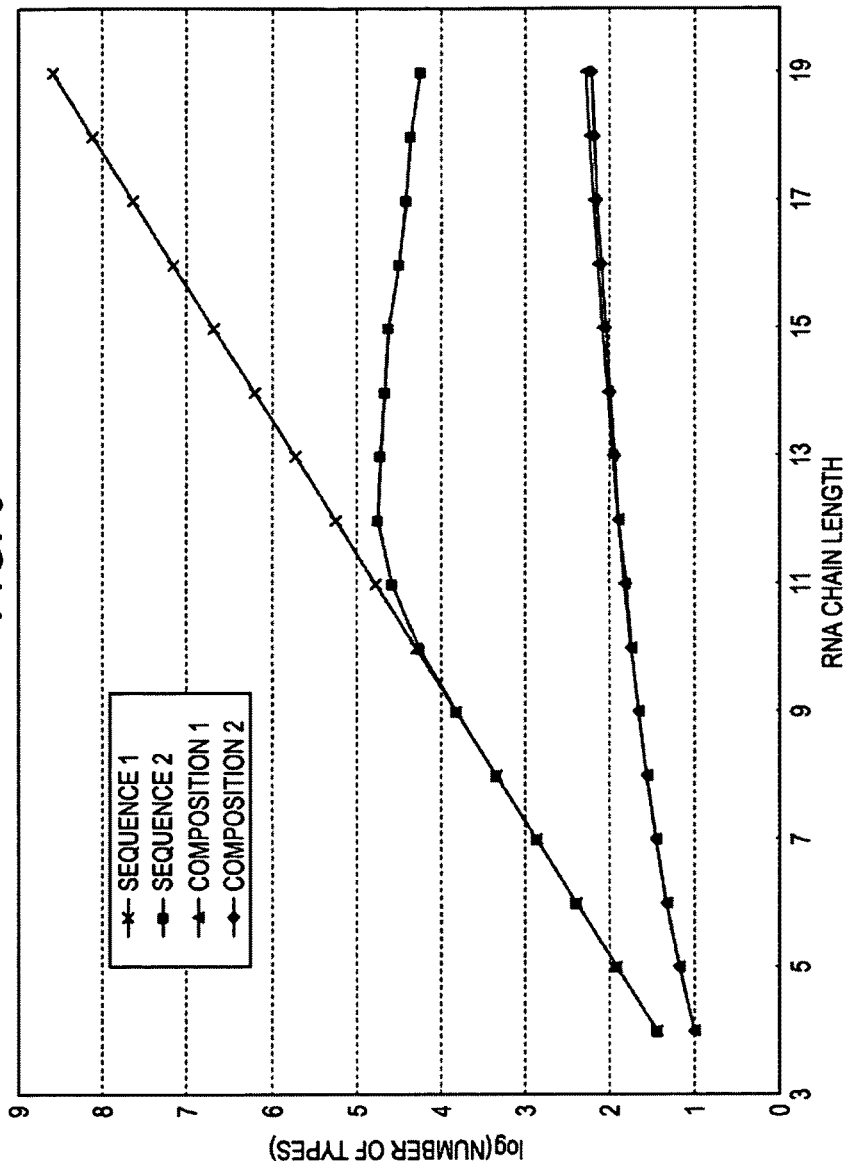
FIG. 9 is a diagram exemplifying the number of types and composition, which are able to be specified to the length.

Here, a difference of the amount of information between sequences and molecular weights will be explained with reference to FIG. 9. A difference of identification capabilities between a conventional method of identifying a location on a genome by using a set of fragment molecular weights and a method of identifying a location on a genome by using a set of fragment sequences according to the present invention will be estimated by a simple calculation.

A database composed of only RNA, ACUGAUCGCUAG, is assumed. Fragment sequences generated when the RNA is digested with RNase T1 are {ACUG, AUCG, CUAG} and the molecular weight of each sequence is 1303.175, which produces {1303.175}, where the 5' terminal of a fragment is OH and the 3' terminal is a cyclic phosphate group. In this example, the three fragments can be identified (distinguished) based on their sequences whereas the three fragments have the same molecular weight and thus cannot be identified based on the molecular weight. Thus, a difference of the capability of the identification between using sequences and using molecular weights can be estimated by comparing the number of possible fragment sequences, generated from a database using set fragmentation conditions, and that of possible fragment molecular weights.

First, RNA fragments that are in principle possible are considered. RNase T1 is assumed as the fragmentation method and it is also assumed that the fragmentation proceeds completely (maximum missed cleavage is 0).

Next, an actual genome is structurally and physiologically biased and thus, all possible sequences in principle do not necessarily appear. Therefore, instead of considering an ideal case, RNase T1 fragment nucleotide that can be generated from the *S. cerevisiae* genome will be considered. Sequences and composition of fragments generated by fragmenting RNA generated by transcribing the genome in both directions by RNase T1 were counted.

In Example 1, the sequence of a fragment nucleotide generated by RNase T1 digestion can be generally represented as (N−1)-time repetition of X and G. Here, X denotes one of A, C, and U residues and N denotes the nucleotide length. In this case, the number of fragment sequences of the length N is given by $3^{N-1}$. The number of the sequences for nucleotide having length of four to nineteen residues is shown in FIG. 9 (Sequence 1). The horizontal axis of FIG. 9 is the length and the vertical axis is the number of types obtained after $\log_{10}$ conversion.

The digestion of the *S. cerevisiae* genome with RNase T1 results in (the generation of) 360726 types of the fragment sequences between four and nineteen residues. FIG. 9 shows the numbers of sequences for these fragments counted for each length (Sequence 2). At the length of 10 or longer, as expected, the number of possible sequences in principle deviated from the number of sequences actually appearing in the genome. Therefore, when the length exceeds 10 residues, the necessary calculation amount of the MS/MS ion search that needs to consider only sequences actually appearing in a genome and derivatives thereof is smaller than that of de novo sequencing that requires consideration of all possible sequences.

Comparative Example

The same case as the above example will be considered. First, the meaning of molecular weight is confirmed. The most meaningful structural information obtained when the molecular weight of a fragment is determined without error is residue composition of the fragment. Thus, for simplicity, the number of fragment residue compositions, instead of that of fragment molecular weights, is used in this comparative example and compared with the number of fragment sequences.

To calculate the number of compositions for the above general RNase T1 fragment sequences, three types of residues {A, C, U} other than G can be considered in a portion of the length (N−1) excluding the 3' terminal G yields the combination (3+N−2)C$_{N-1}$ which is the number of different types obtained by N−1 times trials of choosing a residue from three types of the residues with allowing repetition, where N is the fragment length. FIG. 9 shows the number of compositions for each fragment length of four to nineteen residues calculated from this formula (Composition 1). For all lengths, the example 1 yields larger numbers of sequence types, indicating higher identification capabilities. Moreover, the differences between the number of the sequences and the number of the compositions grow with increasing the length. For the length of about 10 residues, the differences are several hundred-fold.

The digestion of the *S. cerevisiae* genome with RNase T1 results in 1223 types of base composition (1223 types also of the molecular weight) for fragments of four to nineteen residues. Therefore, the numbers of the types of the sequences have on average about 300 times larger than those of the compositions. FIG. 9 shows the numbers of the compositions for these fragments counted for each length (Composition 2). Regarding composition, even when the length is 10 or longer, the deviations of the numbers of possible compositions in principle from those of compositions actually appearing in the genome are small. For any length of eight residues or longer, the number of the sequences is several hundred times larger than that of the compositions.

Example 2

Figure 10:
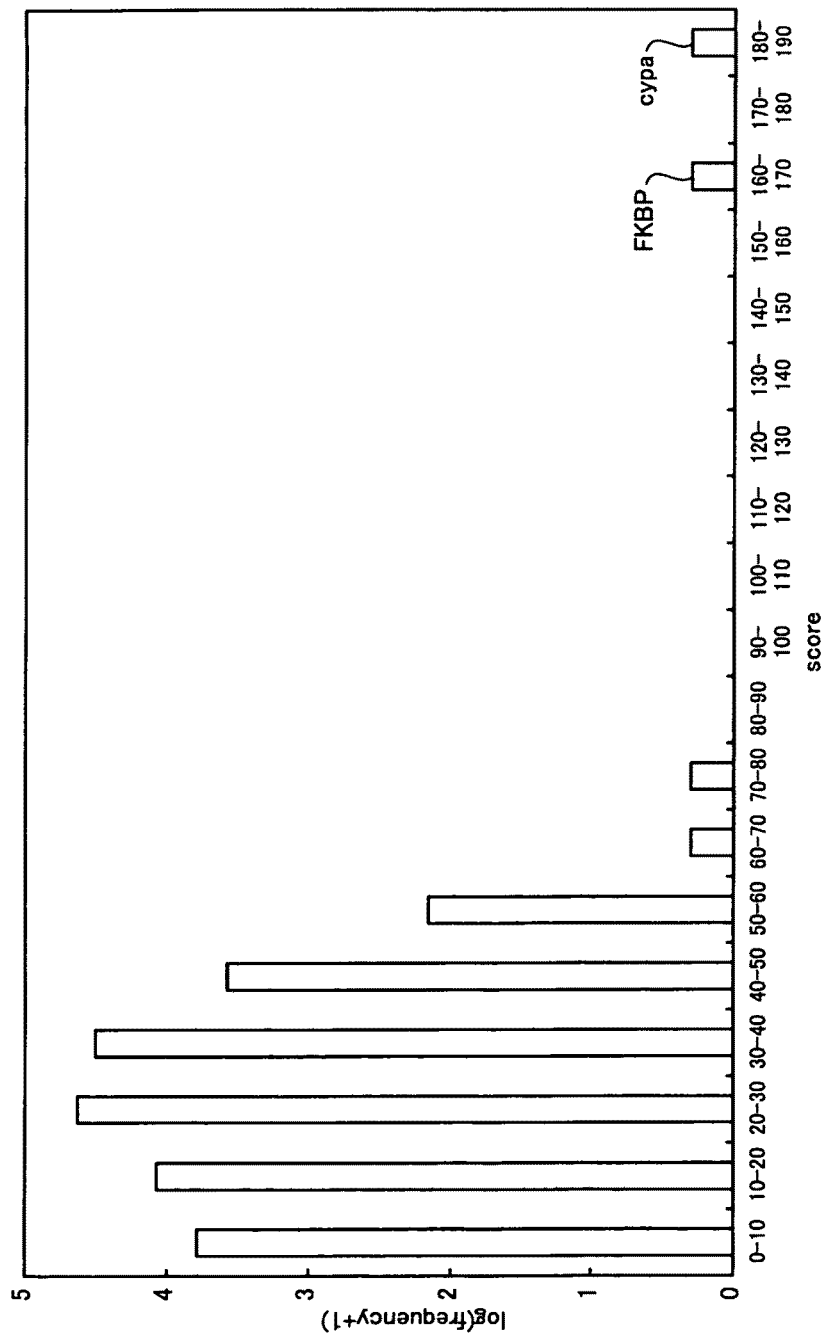
FIG. 10 is a diagram showing an example of a comparison of the results obtained by searching against a merged database.
Figure 12:
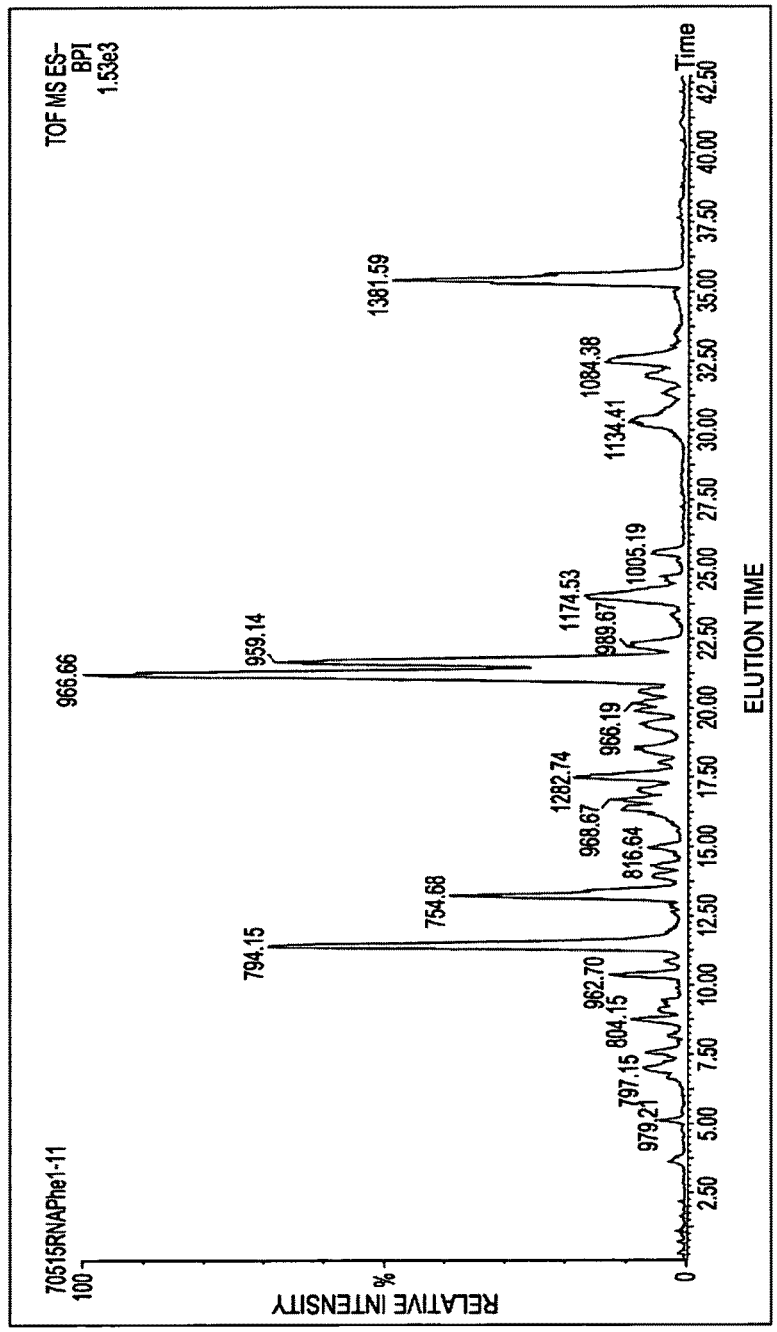
FIG. 12 is an LC-MS/MS chromatogram of RNase T1 digestion product of a tRNA-Phe.
Figure 14:
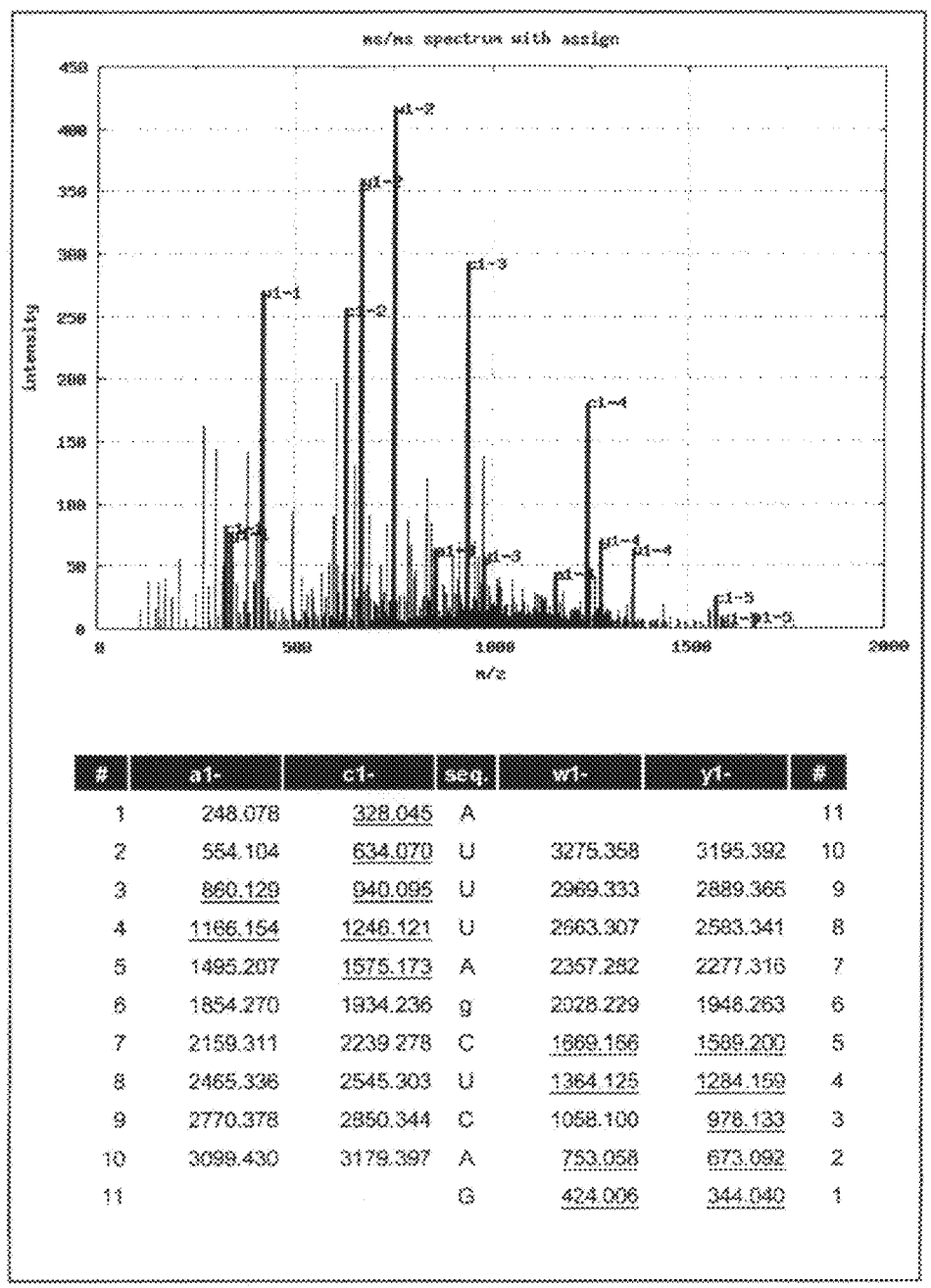
FIG. 14 is a diagram showing an example of the MS/MS spectrum and the assignment of product ions.
Figure 15:
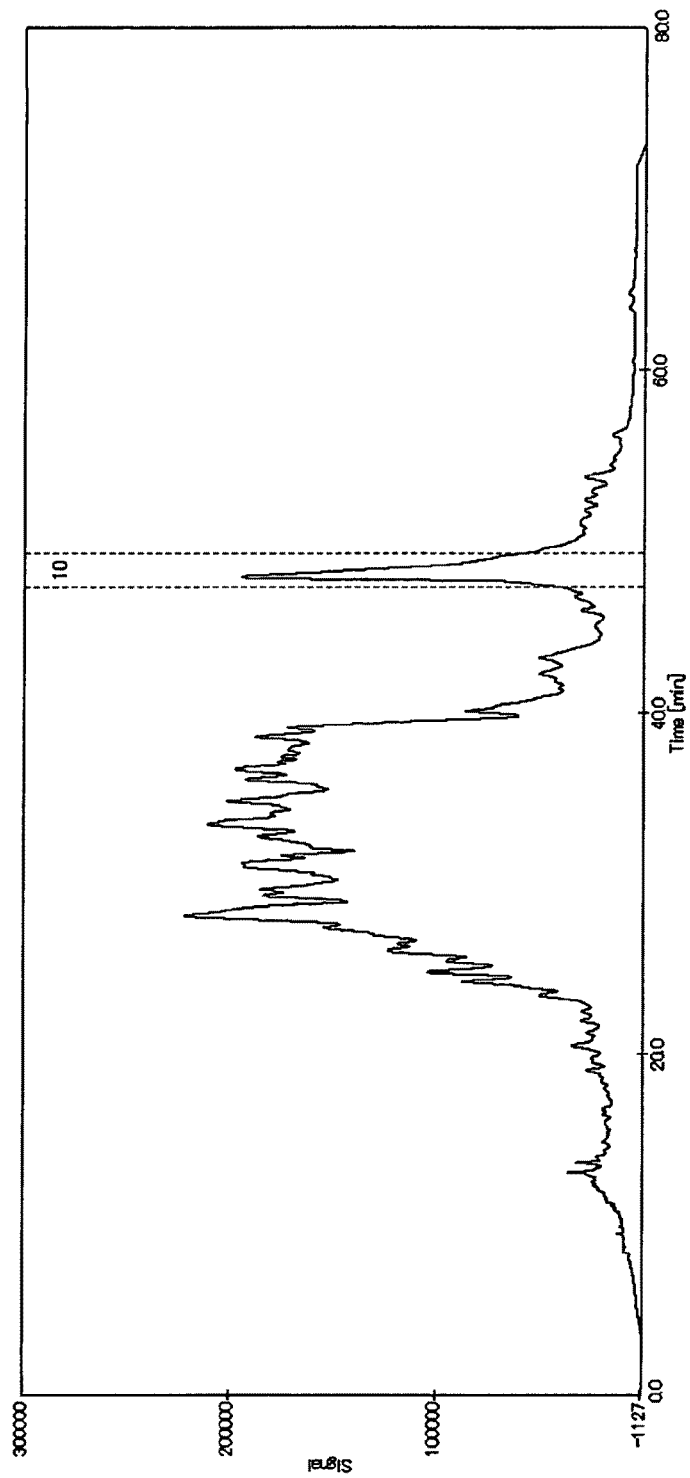
FIG. 15 is a diagram showing fractionation of yeast tRNA using an anion-exchange column.
Figure 16:
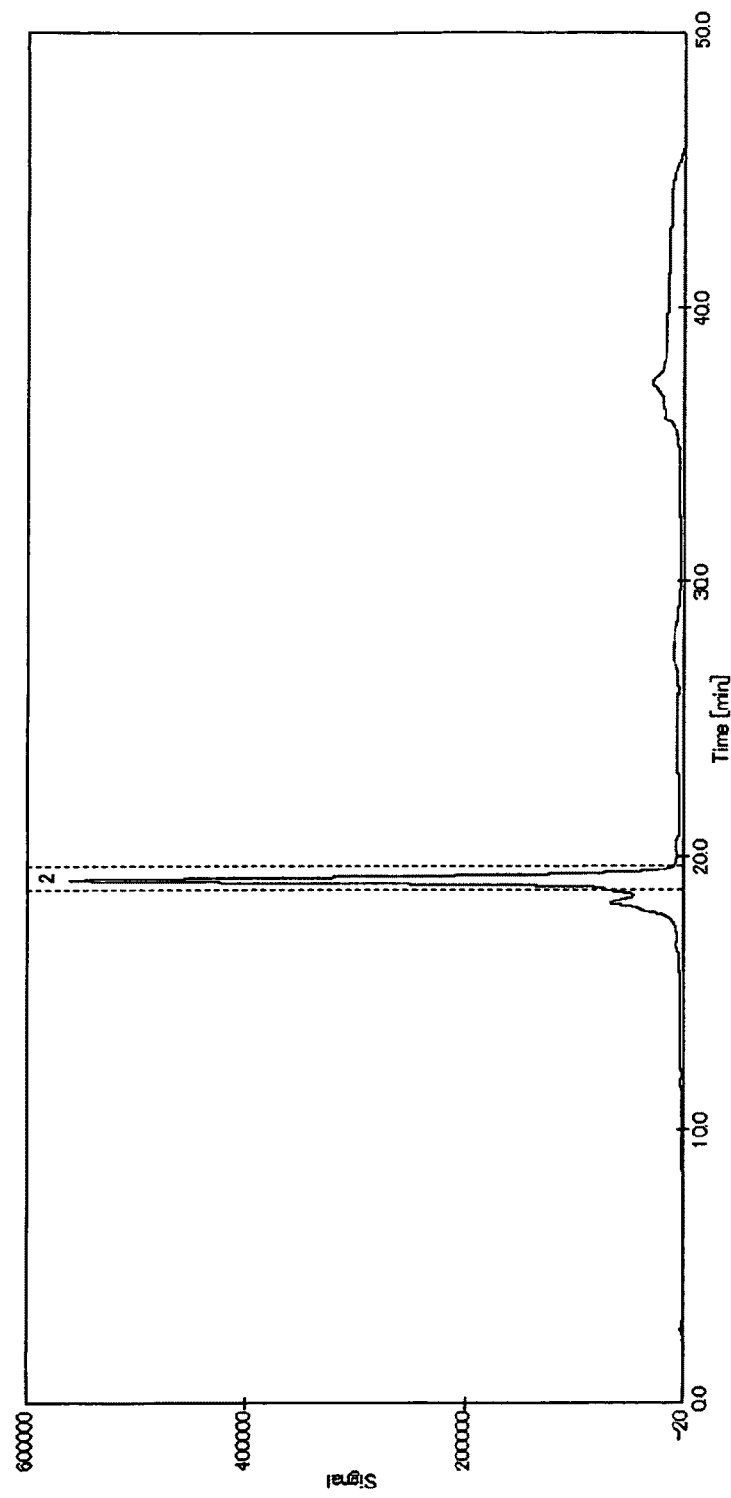
FIG. 16 is a diagram showing desalting purification by reverse phase LC of anion-exchanged fraction No. 10 of yeast tRNA.
Figure 17:
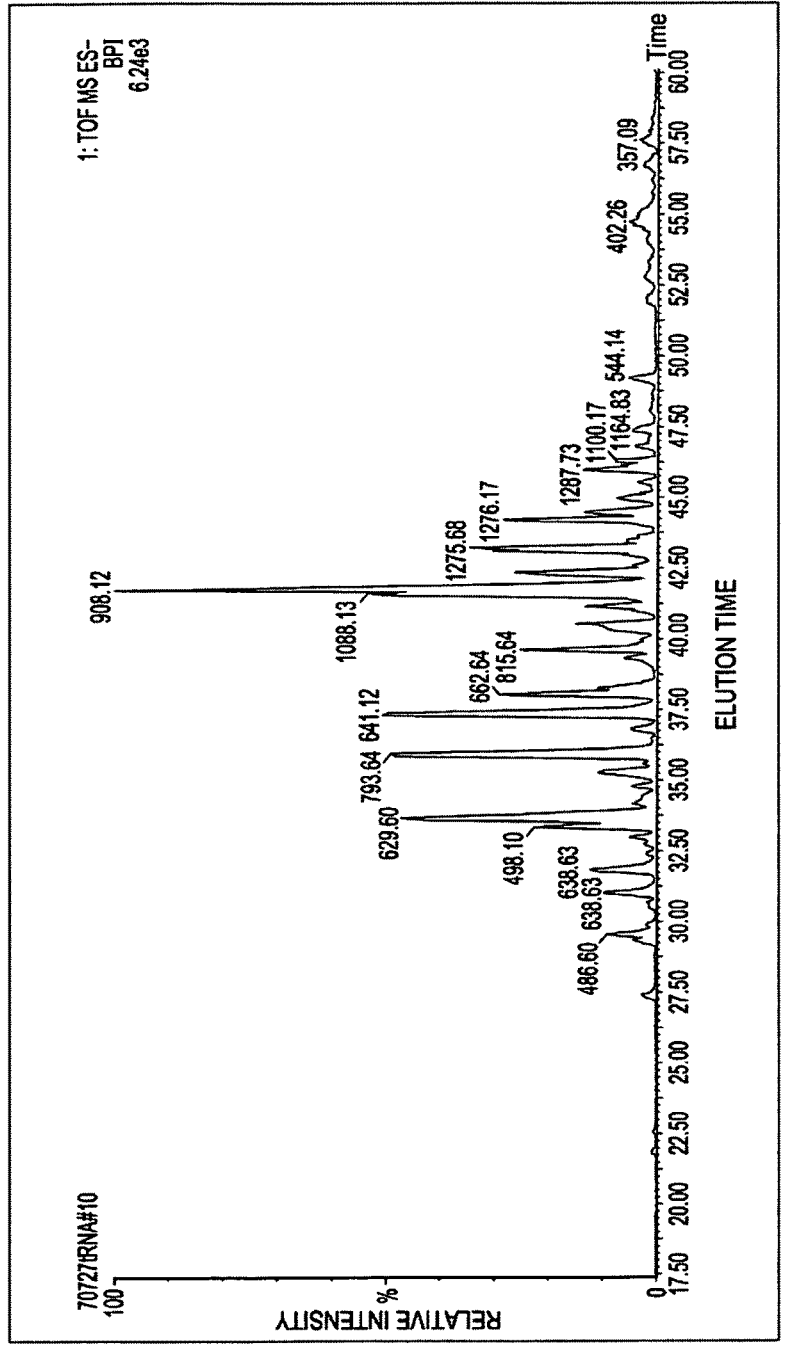
FIG. 17 is an LC-MS/MS chromatogram of the RNase T1 digestion product of fraction 10-2 of a yeast tRNA mixture.
Figure 18:
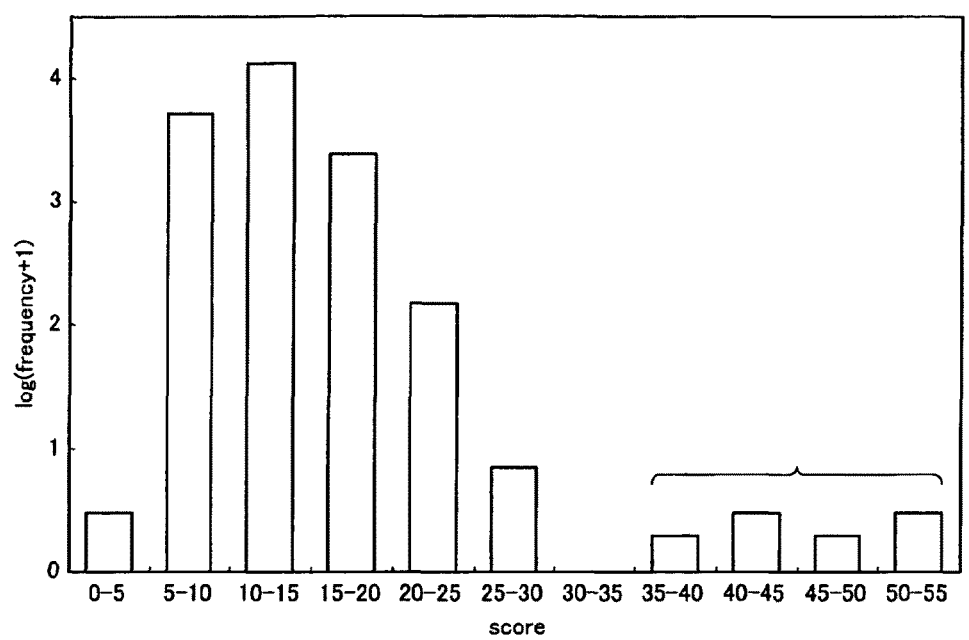
FIG. 18 is a mapping score bar graph showing the search results for the RNase T1 digestion product of fraction 10-2 of a yeast tRNA mixture.

The examples 2-1 to 2-3 concerning the RNA identification apparatus 100 will be explained with reference to FIGS. 10 to 22. FIG. 10 shows a score histogram obtained by searching using an LC-MS/MS result of RNase T1 digest of cell-free (in vitro) transcribed *Xenopus laevis* cyclophilin A (xCyPA) mRNA according to the present invention. FIG. 11 shows a diagram exemplifying comparison of search results against a 'correct-answer' database. FIG. 12 shows an LC-MS/MS chromatogram of RNase T1 digest of tRNA-Phe. FIG. 13 shows a diagram representing search results of tRNA-Phe against a DNA sequence. FIG. 14 shows a diagram exemplifying an MS/MS spectrum and assignments of product ions. FIG. 15 shows a diagram representing a chromatogram of a yeast tRNA mixture preparatively isolated by ion exchange chromatography. FIG. 16 shows a diagram representing a chromatogram of the fraction No. 10 of the anion exchange (as shown in FIG. 15) by reversed-phase LC for desalting/purification. FIG. 17 shows an LC-MS/MS chromatogram of RNase T1 digest of the fraction 10-2 (as shown in FIG. 16). FIG. 18 is a score histogram of search results of yeast tRNA mixture fraction 10-2 RNase T1 digest. FIGS. 19 to 22 show diagrams exemplifying sequence regions identified by mapping.

<Materials/Methods>

Here, materials and methods used in the Examples 2-1 to 2-3 are shown in (1) to (9) below:

(1) In Vitro Transcription

In the Example 2-1, *Xenopus laevis* Cyclophilin A (CyPA) cDNA (reflNM_001089190.1l) or *Xenopus laevis* FK506 binding protein (xFKBP) gene inserted into the 3' untranslated region (UTR) of a globin gene in a pBluescript RN3 vector (provided by Dr. Makoto Asashima) was prepared by using an in vitro transcription kit of Ambion (company name). Then, the prepared pBluescript RN3-xCyPA vector or pBluescript RN3-XFKBP vector was used as a template to synthesize mRNA containing an xCyPA sequence or xFKBP sequence in a globin derived sequence in a cell-free transcription system. The synthesized mRNA was purified by a QIAGEN RNeasy kit (trade name) and the purity thereof was confirmed by the polyacrylamide gel electrophoresis.

(2) RNA

In Examples 2-2 and 2-3, an *S. cerevisiae* tRNA-Phe and a mixture of yeast tRNAs (tRNA typeX, from baker's yeast) were purchased from Sigma (company name). Ribonuclease T1 (RNase T1) was purchased from Worthington (company name).

(3) Purification of Unknown RNA by Ion Exchange Chromatography

In Example 2-3, 100 μg of tRNA mixture was isolated by ion exchange chromatography to preparatively isolate each peak (FIG. 15). Then, a fraction near 48 min (fraction 10 in FIG. 15) was further purified by reversed-phase HPLC. The fraction (a fraction 10-2 in FIG. 16) was stored at −20° C. after removing a solvent by lyophilization or ethanol precipitation.

(4) RNase T1 Digestion

RNase T1 was purified by reversed-phase liquid chromatography in order to remove ammonium sulfate and lyophilized. Then, the lyophilized enzyme was re-dissolved by DNase/RNase-free sterilized water (invitrogen (company name)). After dissolving the sample RNA in a digestion buffer solution (10 mM ammonium acetate buffer (pH 5.3)) to prepare 0.25 μg/μL thereof, 1/500 amount (weight/weight) of RNase T1 was added for fragmentation at 37° C. for 30 min. The resulting enzymatic digests were immediately analyzed by liquid chromatography-tandem mass spectrometry (LC-MS/MS).

(5) LC-MS/MS Analysis

For LC-MS/MS, a nanoflow LC-MS/MS system for proteomics (T. Natsume et al. Anal. Chem. 2002, 74, 4725-4733) was used. However, the system was modified for RNA for each item (a) to (d) shown below:

(a) Column packing material: Develosil C30-UG-3 (Nomura Chemical (company name)), column size: 100 μmID×50 mL (b) Solvent A: 10 mM triethylamine-acetic acid solution (TEA-AA) pH 7.0, B: methanol (MeOH)

(c) Elution condition: performed using a 60-min linear gradient from 10% to 40% solvent B at a flow rate of 100 nL/min (d) Mass spectrometer: Q-T of Ultima (Waters (company name)), ionization voltage: −1200 V (negative mode), measured mass range (m/z): 400 to 1600

(6) MS/MS Ion Search

A peak list was created from LC-MS/MS analysis results using MassLynx (Waters (company name)) and SpiceCmd (Mitsui Knowledge Industry (company name)).

(7) Search conditions for *Xenopus Laevis* Synthetic mRNA

In the Example 2-1, a nucleic acid sequence DB containing only xCyPA and xFKBP sequences (correct-answer DB) or a nucleic acid sequence DB (merged DB) in which xCyPA and xFKBP sequences were added to the human Reference Sequence (RefSeq_human (Reference Sequence release 27, 2008-02-18 download, *H. sapiens* 38, 864 entries)) was searched for LC-MS/MS analysis results of xCyPA and xFKBP synthetic mRNA. It is noted that no mRNA having significant homology could not be detected by the blast search against the human Reference sequence using xCyPA and xFKBP sequences as queries, confirming that the DB can be used to judge whether false positive occurs when identifying xCyPA and xFKBP. That is, all MS/MS can identify xCyPA or xFKBP as top rank. In the present embodiment, the assignments in an MS/MS spectrum of nucleotides identified by the search against the DB containing only xCyPA and xFKBP were validated by the visual inspection of researchers. Next, by the data set, the merged database was MS/MS-ion-searched and the identified nucleotides were mapped to the merged database. If any entry derived from the human Reference sequence was identified by mapping, the entry was determined to be incorrect.

(8) Search Conditions for *S. Cerevisiae* tRNA-Phe

In Example 2-2, an *S. cerevisiae* tDNA sequence downloaded from Genomic~tRNA db (http://lowelab.ucsc.edu/GtRNAdb/) was used as a nucleic acid sequence DB for tRNA. For modification conditions, methylation to four types of bases ACGU or sugar 2'OH and reduction of U to dihydro-U were considered. The maximum number of modifications that can be occurred at the same time for one fragment was set to be "2". The maximum number of missed cleavages was set to be "2". If fragment sequences containing modifications were identified by the MS/MS ion search, mapping to the nucleic acid sequence DB was performed after modifications were removed from these fragment sequences to restore the original sequences. If, as a result of removing modifications, missed cleavage fragments were generated, these fragments were converted into a set of completely digested fragments before mapping.

(9) Search Conditions for *S. Cerevisiae* tRNA Mixture

In Example 2-3, *S. cerevisiae* genomic sequence downloaded from mNCBI (ftp://ftp.ncbi.nih.gov/genomes/Fungi/Saccharomyces_cerevis iae/) was used as a nucleic acid sequence DB for a mixture. The search was performed by ignoring fragments of three residues or less in length, setting the subentry size to 100 fragments, and not considering missed cleavages and modifications.

<Results>

Results shown in the Examples 2-1 to 2-3 below were obtained by using the above materials and methods.

Example 2-1

Validation of the MS/MS Ion Search Using a Cell-Free Transcribed mRNA and Application of the MS/MS Ion Search to a Mixture A nucleic acid sequence DB containing only xCyPA was searched for a peak list extracted from LC-MS/MS data of RNase T1 digests of xCyPA mRNA. As a search parameter, the maximum number of missed cleavages for digestion was set to "0" or "2".

By the MS/MS ion search in the present invention, the same 66 types of fragments were identified when the maximum number of missed cleavages was set to be "0" or "2". All 66 types were determined to be correct by researchers who inspected the selection of monoisotopic peaks of precursor ions of fragments corresponding to the identified fragment sequence list, charges of the precursor ions, and assignments of main product ions. In calculation, 87 types of fragments can be generated when xCyPA is digested with RNase T1; however 75 types of these 87 fragments are with at least four residues and within the LC-MS/MS measured mass range. Therefore, the correct identification included 88% of the total number.

A result of searching these fragments against the merged DB showed that 1. no change (xCyPA was identified as top rank) occurred for 57 types, 2. identification due to a rising threshold with an increasing size of the database for 0 type, and 3. identification of a sequence other than xCyPA for nine types.

Here, a two-step search to map to the nucleic acid sequence DB by the entry scoring section $102p$ and the entry identification section $102q$ was performed using the identified fragment sequence list created by the above mass (MS/MS) search. By performing the two-step search (first step: assignment to the fragment, second step: mapping to the nucleic acid sequence DB), RNA could be correctly identified in the second step even if the results of the MS/MS ion search in the first step included an incorrect one.

Similarly, as a result of searching the DB containing only xFKBP for a peak list extracted from LC-MS/MS data of RNase T1 fragments of xFKBP, 80% or more sequence coverage was obtained. Next, the two-step search of the merged DB was similarly performed and, like xCyPA, even if an incorrect result was contained in the MS/MS ion search in the first step, xFKBP could be identified correctly.

Next, whether the present invention can be applied effectively to a mixture was examined.

The peak lists of each one of the two genes were mixed to create a new peak list to be used for the present evaluation.

It was expected that by analyzing search results using the peak list against the merged DB, the capabilities to distinguish between the two correct identifications in a mixture sample and between correct and incorrect identifications in the mixture sample can be evaluated.

FIGS. 10 and 11 show results of identifying xCyPA and xFKBP from the mixture of the both by searching against the merged DB. FIG. 10 shows a mapping score histogram in which the horizontal axis is the mapping score and the vertical axis is the score frequency obtained after $\log_{10}$ conversion. FIG. 11 represents, for each of CyPA and FKBP, the mapping score, number of identified fragments, number of fragments that can be generated by the specified fragmentation method (RNase T1 in the present example), and fragment numbers indicating the location where an identified fragment is generated in RNA. It should be noted that a sequence derived from globin is contained in both CyPA and FKBP transcripts and is duplicated in both transcripts so that a common portion of fragment oligonucleotide derived from globin cannot be distinguished in the mixture; however there is no significant homology between original sequences of CyPA and FKBP genes. Therefore, each RNA could be identified even in the mixture of RNAs containing a homologous portion by using the two-step search in the present invention.

Example 2-2

Identification of tRNA-Phe of *S. Cerevisiae* by Searching the Genome Sequence Database for Under a Condition Accompanying Modifications Details of results of examining a posttranscriptional-modified sample are shown below as the Example 2-2. Functional RNAs are frequently subject to modifications post-transcriptionally such as methylation. These modifications play important roles in some cases for functions of RNAs to be expressed and it is desirable that RNA analytical methods can identify modified sequences. The present example shows that by setting a modification table (a table of a modification type corresponding with its mass value) and the maximum number of permissible modifications, a modified sequence generated dynamically during a search can be matched with measured data even when searching a nucleic acid sequence DB which contains no modification information like a DNA sequence database. An example of analyzing tRNA-Phe of *S. cerevisiae* under conditions accompanying modifications will be shown below.

At first, to estimate an appropriate modification parameter as a search condition for the present search, the type of modification and the frequency thereof were surveyed. TRNAs, known to be the most frequently modified RNA, were chosen to survey and sequence information of tRNAs including modifications was acquired from the tRNA complication DB. RNase T1 fragmented oligonucleotides obtained from every tRNA sequence (in the DB) were used after duplicated oligonucleotide was unified.

As a result, 232 types of target nucleic acid sequences were obtained for *E. coli* and 229 types for *S. cerevisiae*. The oligonucleotides were classified according to classification rules (a) to (c) below (see the table below):

(a) Non-Modification or No Mass Shift

Modifications that can be detected by mass spectrometry are only those causing mass shifts and thus the most frequent modification type, pseudouridine, was put into the same classification as normal bases without modification.

(b) Methylation and Reduction of Uridine to Dihydrouridine

The next most frequent modification types were methylation and reduction of uridine to dihydrouridine in this order. To specify a number of modifications as a search parameter, instead of specifying the upper limit for each modification, it is desirable to be able to specify it as the total number of modifications. Thus, these modifications were handled together and classified according to the total number thereof.

(c) Others

Modifications other than pseudouridilation, methylation, and reduction of uridine to dihydrouridine were handled together and the total number thereof was classified as Others.

TABLE 1

(Classification of tRNA-Phe RNase T1 digests according to posttranscriptional modification)

| Species: | E. coli | S. cerevisiae |
|---|---|---|
| Unmodified, no mass change: | 149 | 101 |
| Modification*number 1: | 24 | 64 |
| Modification*number 2: | 5 | 24 |
| Modification*number 3: | 2 | 4 |
| Modification*number 4: | 0 | 1 |
| Other modifications: | 52 | 35 |

(*methylation and reduction of uridine to dihydrouridine)

While the modification types and the number thereof are different depending on the species, if no modification, pseudouridilation, methylation, and reduction of uridine to dihydrouridine are considered as the modification types and if the maximum number of methylation and reduction of uridine to dihydrouridine is specified to be "2", 178 types (77% of the total) are included for *E. coli* and 189 types (83% of the total) for *S. cerevisiae*. Thus, the condition was considered to be sufficient for tRNA identification. That is, even if the maximum number of modifications is increased to "3", "4" or the like, the number of sequences that can be handled hardly increases whereas the calculation amount increases rapidly. These surveys can conclude that the maximum number of modifications of "2" was sufficient for the identification. To handle sequences containing more modifications, it can be useful that a search with more modifications is performed against a limited search target including only the RNA sequences identified by a search against a normal database with consideration of methylation and reduction of uridine to dihydrouridine as the target modification type and with the maximum number of the modifications "2" as a search parameter.

Missed cleavage fragments would be generated accompanying a modification at a cleavage site (many modification bases are not recognized by RNase) and the maximum number of permissible missed cleavages thus has to be specified as a search parameter. For this search condition, it is preferable to set the parameter value equal to or larger than the maximum number of modifications according to digestion conditions.

As a result of the above survey, the conditions for the present search were determined that the modification type to be considered was methylation and reduction of uridine to dihydrouridine, that the maximum number of modifications was "2", and that the maximum number of permissible missed cleavages was "2" (as the maximum number of modifications).

Subsequently, commercial tRNA-Phe was digested with RNase T1 and 500 fmol of the digest were subjected to LC-MS/MS measurement (see FIG. 12). The obtained MS/MS spectra were identified by visual inspection of researchers against a tRNA-Phe derived sequence (see FIG. 13). Then, these MS/MS peak lists are defined as an evaluation-peak-list set.

As the nucleic acid sequence DB to be searched, 72 types of unique sequences were obtained among 275 types regarding *S. cerevisiae* tRNAs acquired from the genomic tRNA database (http://lowelab.ucsc.edu/GtRNAdb/) by organizing the same sequence into the same nucleic acid sequence entry. The nucleic acid sequence DB was searched using the evaluation-peak-list set. Main search conditions were listed as follows: the maximum mass error (precursor ions) to "500 ppm", the maximum mass error (product ions) to "500 ppm", the maximum number of modifications to "2", nuclease to "RNase T1", the maximum number of missed cleavages to "2", and the minimum number of nucleotide to be considered to "four bases or more".

FIG. 13 shows a list of the fragment sequences obtained by RNase T1 digestion of an RNA sequence transcribed from the DNA sequence of the tRNA-Phe gene. As shown in FIG. 13, identified missed cleavage fragments are shown together with all the completely digested fragments. The spliced-out sequence accompanying a wybutosine (yW) modification is explained as comments. The identified fragments by the visual inspection of the MS/MS spectra were indicated by a circle or a double circle and were 12 nucleotides. Among these fragments, 10 types excluding the site 25-30 (including dimethylation) and the site 31-60 (including cleavage/reconnection of sequence and yW) were within the scope of the search of the present example. Among these 10 nucleotide types, nine could be identified. Six fragments (five modification sites) included modification (s) out of the 9 identified nucleotides.

As shown in FIG. 13, the nucleotide that could not be identified in the Example 2-2 is $^{64}$GUCCU$^{69}$G ($^{64}$m$_7$G). The nucleotide has peak with weak intensity in LC-MS and quality of MS/MS spectrum is poor. The modified residue, m$_7$G, is known to have a positive charge in neutral pH so that the ionization efficiency of a nucleotide containing m$_7$G or the generation efficiency of its product ions is lower than that of normal nucleotide, which may be a reason that the nucleotide could not be identified.

FIG. 14 shows the MS/MS spectrum (upper figure) from which the sequence AUUUAGCUCA (site: 5-15, methylation of $^{10}$G) including modifications was identified by the MS/MS ion search in the present invention and assignment of product ions (lower figure). In FIG. 14, the mass value of each product ion estimated from the identified sequence is shown. For example, #1 of the $c^{1-}$ series ($^{1-}$ represents a singly charged ion in negative mode) shows that the theoretical product ion mass value of the product ion of $c^{1-}_1$ is "328.045".

An underline in the theoretical product ion table in FIG. 14 indicates matching with the value of the measured product ion mass extracted from the MS/MS spectrum. As the result shows, for example, mass values of product ions of $c^{1-}_1$ to $c^{1-}_5$ from the 5' side were matched and, on the other hand, mass values of product ions of $y^{1-}_1$ to $y^{1-}_7$ from the 3' side were matched, which shows that the sixth G from the 5' side is subject to a modification. That is, methylation of the sixth G of the identified AUUUAGCUCAG was determined.

In this manner, a search using MS/MS spectral data allows to identify not only presence/absence of modification, but also the modification site. The sixth G (the tenth in the whole tRNA) is known to be 2-methylated, which was confirmed from the result of the above MS/MS spectrum search (see the reference "McLaughlin L W, Cramer F, Sprinzl M." Rapid analysis of modified tRNAphe from yeast by high-performance liquid chromatography: chromatography of oligonucleotides after RNase T1 digestion on aminopropylsilica and assignment of the fragments based on nucleoside analysis by chromatography on C18-silica. "Anal Biochem. 1981 Mar. 15; 112 (1):60-9").

As explained above, the Example 2-2 revealed that the modification site (s) can be identified together with the RNA by searching against a nucleic acid sequence DB for a sample containing a posttranscriptional modification. That is, according to Example 2-2, by making conversions between a modified sequence and an unmodified sequence in fragment sequences by referring to stored modification rules, the presence of a posttranscriptional modification in an RNA contained in a sample can be detected by the search of a sequence database containing no modification and also the modification site thereof can be determined.

Example 2-3

Identification by Searching Against a Genome Sequence Database for Unknown RNA in an *S. Cerevisiae* tRNA Mixture Subsequently, the Example 2-3 in which an unknown sample in a tRNA mixture was identified will be shown. The unknown RNA is an RNA contained in a commercial tRNA mixture and is clearly different from tRNAs in size. To identify the unknown RNA, a genome sequence database was searched.

FIG. 15 shows an elution profile ($A_{260}$) of a mixture of yeast (*S. cerevisiae*) tRNA by ion exchange chromatography. A large proportion of RNA was eluted as lumps in about 22 to 45 min. These lumps are considered to tRNAs having mutually similar structures. On the other hand, as shown in the fraction 10 of FIG. 15, a peak was also detected near 48 min. Since it is known that ion exchange chromatography has larger retention with an increasing length of nucleic acid, the RNA in the fraction 10 was estimated to be larger than the usual tRNAs.

Next, the fraction 10 was preparatively isolated and further purified by reversed-phase chromatography (the fraction 10-2 in FIG. 16). The peak component has a decreased mobility as compared with usual tRNAs on electrophoresis (that is, the larger molecular weight). This result supports the result of ion exchange chromatography.

From the above, the fraction 10-2 was considered to be an RNA other than tRNA contaminated in the tRNA mixture. The fraction was digested with RNase T1 and the resulting digest was analyzed by LC-MS/MS. FIG. 17 shows an LC-MS/MS chromatogram of the digest.

Then, MS/MS ion search and mapping to a tRNA nucleic acid sequence DB were performed by the MS/MS peak list of the unknown RNA, but, as expected, no significant identification result could be obtained. Then, MS/MS ion search and subsequent mapping were performed against the *S. cerevisiae* genome sequence. Here, each chromosome of the genome was divided into subentries and each subentry contains unique 100 fragments excluding duplication.

As a result, as shown in FIG. 18, six subentries of chromosome XII were identified with significantly high scores (in the range of the mapping score 35 to 55 in FIG. 18 with the vertical axis in $\log_{10}$). By comparison, sequences located near these identified subentries showed high homologies with one another. The blast search against NCBInr using genomic regions where fragments are continuously identified as a query indicated 5S rRNA (gi|176405|).

Conversely, the blast search against the *S. cerevisiae* genome sequence performed using the 5S rRNA sequence (sequence number 1) as a query detected six sequence regions in chromosome XII where the homologies are 98% or more (sequence numbers 2 to 7 in this order) as shown in FIGS. 19 to 22. These sequence regions are consistent with those identified by mapping of the MS/MS ion search results. 5S rRNA is about 120 residues in length, which is longer than usual tRNA (70 to 80 residues), which is also consistent with the results of the chromatography and the electrophoresis.

According to Example 2-3, as explained above, it was revealed that the location of an unknown RNA on a genome can be determined by using MS/MS ion search results. Thus, being able to identify RNA by searching against a large database of genome or the like is extremely useful in the field of search/identification of RNA where, in contrast to proteins, databases are not yet well developed and maintained and the RNA identification apparatus 100 is shown to achieve an advantageous effect.

Example 3

Next, an example of an RNA identification system in which the RNA identification apparatus 100 is set as a server apparatus 400 and the server apparatus 400 is configured to return an identification result to a client apparatus 200 will be explained with reference to FIG. 23. The RNA identification apparatus 100 may be communicably connected to a network via a communication apparatus such as a router and a wire or wireless communication line such as a leased line.

The RNA identification system according to the present example is constituted of the client apparatus 200 and the server apparatus 400. These apparatuses are communicably connected by wire or wireless via a network 300. The client apparatus 200 includes a control section 202 including a peak acquisition section 202a, a search condition input section 202p, and a result output section 202q, a storage section 206 that stores peak lists, search results, and result reports, an input section 212, and an output section 214. The client apparatus 200 acquires tandem mass spectrometry data (mass spectrometry data generated by a tandem mass spectrometer 10) through the control section 202. The server apparatus 400 includes a control section 402 and a storage section (internal DB) 406 and is communicably connected to an external database (nucleic acid sequence DB) 500 that stores nucleic acid sequences for each nucleic acid entry by wire or wireless via a network 600.

Figure 23:
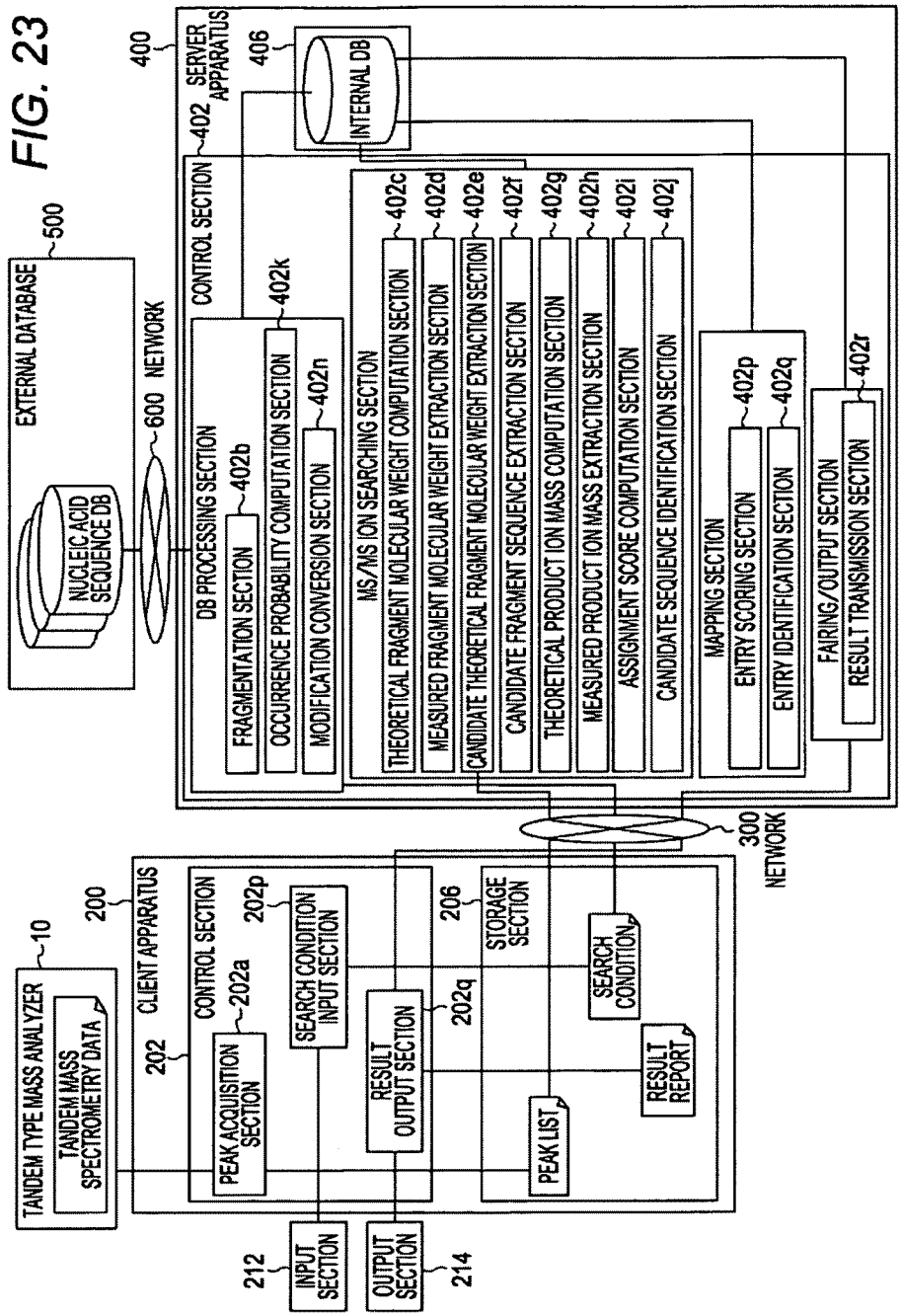
FIG. 23 is a block diagram showing an example of the configuration of the present system for RNA identification to which the present invention is applied.

Here, excluding the search condition input section 202p, the result output section 202q, and the result transmission section 402r, each section shown in FIG. 23 is common to each section having the same name shown in FIG. 2 and thus, in the present example, the explanation of these common sections is omitted.

The search condition input section 202p is set up as a unit to execute the means for storing search conditions (specifying at least the residue-sequence-specific-cleavage method or the like) input via the input section 212 in the storage section 206 and also to send the search conditions to the server apparatus 400. The result output section 202q is set up as a unit to execute the means for storing an identified fragment sequence list (including identified fragment sequences, which are fragment sequences identified by a candidate sequence identification section 402j) sent from the server apparatus 400 in the storage section 206 as a result report and also to output the result report via the output section 214.

The control section 402 is constituted of a DB processing section, an MS/MS ion searching section, a mapping section, and a fairing/output section. The DB processing section includes a fragmentation section 402b, an occurrence probability computation section 402k, and a modification conversion section 402n. The MS/MS ion searching section includes, as illustrated in FIG. 23, a theoretical fragment molecular weight computation section 402c to the candidate sequence identification section 402j. The mapping section includes an entry scoring section 402p and an entry identification section 402q. The fairing/output section includes the result transmission section 402r. The result transmission section 402r is set up as a unit to execute the means for sending an identified fragment sequence list to the client apparatus 200.

Next, processing performed in the RNA identification system according to the present example configured as explained above will be explained below.

First, the peak acquisition section 202a creates a peak list by extracting peaks from tandem mass spectrometry data concerning the identification target RNA cleaved by the residue-sequence-specific-cleavage method (for example, an enzymatic cleavage method by nuclease or a chemical cleavage method) and stores the created peak list in the storage section 206 and also sends the peak list to the server apparatus 400. The search condition input section 202p stores search conditions input via the input section 212 in the storage section 206 and also sends the search conditions to the server apparatus 400.

Then, the fragmentation section 402b reads a nucleic acid sequence contained in a nucleic acid sequence entry list stored in the external database 500 via the network 600. Then, the fragmentation section 402b fragments the read nucleic acid sequence based on search conditions sent from the client apparatus 200 by referring to the fragmentation rule (corresponding to the residue-sequence-specific-cleavage method) stored in the storage section 406 to create a fragment sequence list including fragment sequences of the nucleic acid sequence. Here, as processing of the DB processing section, the occurrence probability computation section 402k may calculate occurrence probabilities of fragment sequences of a nucleic acid sequence in a subset specified in advance as a search target from the nucleic acid sequence list stored in the external database 500. Also as processing of the DB processing section, the modification conversion section 402n may make conversions between a modified sequence and an unmodified sequence in fragment sequences by referring to modification rules. More specifically, the modification conversion section 402n may add a modification to a nucleic acid sequence without modification (generate a fragment sequence to which a modification is added based on modification rules for each fragment sequence) or remove a modification from an identified modification-added fragment sequence to identify the nucleic acid entry by associating the identified fragment sequence with the sequence of the original nucleic acid entry.

Then, the theoretical fragment molecular weight computation section 402c calculates the theoretical fragment molecular weight for all fragment sequences of the fragment sequence list created by the fragmentation section 402b to create a theoretical fragment molecular weight list containing the theoretical fragment molecular weight. On the other hand, a measured fragment molecular weight extraction section 402d creates a measured fragment molecular weight list containing the measured fragment molecular weights by extracting the measured fragment molecular weight of each peak from the peak list sent from the client apparatus 200.

Then, a candidate theoretical fragment molecular weight extraction section 402e compares the theoretical fragment molecular weight contained in the theoretical fragment molecular weight list created by the theoretical fragment molecular weight computation section 402c and the measured fragment molecular weight contained in the measured fragment molecular weight list created by the measured fragment molecular weight extraction section 402d to extract a candidate theoretical fragment molecular weight corresponding to the measured fragment molecular weight of each peak to create a candidate theoretical fragment molecular weight list containing the candidate theoretical fragment molecular weight.

Then, a candidate fragment sequence extraction section 402f extracts a candidate fragment sequence, which is a fragment sequence corresponding to each candidate theoretical fragment molecular weight contained in the candidate theoretical fragment molecular weight list created by the candidate theoretical fragment molecular weight extraction section 402e, from the fragment sequence list created by the fragmentation section 402b to create a candidate fragment sequence list (including the candidate fragment sequence) corresponding to each peak.

Then, a theoretical product ion mass computation section 402g calculates the theoretical product ion mass corresponding to each product ion generated according to a predetermined dissociation rule for each fragment sequence contained in the fragment sequence list created by the fragmentation section 402b to create a theoretical product ion mass table containing the theoretical product ion mass. On the other hand, a measured product ion mass extraction section 402h extracts the measured product ion mass from each peak of the peak list sent from the client apparatus 200 to create a measured product ion table containing the measured product ion mass.

Then, an assignment score computation section 402i compares the theoretical product ion mass contained in the theoretical product ion table created by the theoretical product ion mass computation section 402g and the measured product ion mass contained in the measured product ion table created by the measured product ion mass extraction section 402h to assign a score to all candidate fragment sequences contained in the candidate fragment sequence list created by the candidate fragment sequence extraction section 402f.

Then, the candidate sequence identification section 402j identifies the fragment sequence of RNA to be identified from a candidate fragment sequence contained in the candidate fragment sequence list created by the candidate fragment sequence extraction section 402f based on the score assigned to all candidate fragment sequences by the assignment score computation section 402i to create an identified fragment sequence list containing an identified fragment sequence, which is the fragment sequence that is identified. The entry scoring section 402p may compare each identified fragment sequence contained in the identified fragment sequence list created by the candidate sequence identification section 402j and the nucleic acid sequence stored in the external database 500 to assign a mapping score to each nucleic acid entry based on occurrence probabilities of fragment sequences calculated by the occurrence probability computation section 402k so that the entry identification section 402q can identify the most probable nucleic acid entry based on the assigned mapping score.

The result transmission section 402r sends the identified fragment sequence list created by the candidate sequence identification section 402j to the client apparatus 200. The result transmission section 402r may also send processing results of the entry identification section 402q to the client apparatus 200.

Then, the result output section 202q outputs the identified fragment sequence list sent from the server apparatus 400 via the output section 214. The result output section 202q may also output processing results of the entry identification section 402q sent from the client apparatus 200 via the output section 214.

V. Other Embodiments

The embodiments of the present invention have been described above. However, the present invention may be executed in not only the embodiment described above but also various different embodiments within the technical idea described in the scope of the invention. For example, of each of the processes explained in the embodiments, all or some processes explained to be automatically performed may be manually performed. Alternatively, all or some processes explained to be manually performed may also be automatically performed by a known method. In addition, the procedures, the control procedures, the specific names, the information including parameters such as registered data for each of the procedures or the search condition, examples of screen image and the database configurations which are described in the literatures or the drawings may be arbitrarily changed unless otherwise noted.

With respect to each of the above-mentioned devices, the constituent elements shown in the drawings are functionally schematic. The constituent elements need not be always physically arranged as shown in the drawings. Furthermore, a specific configuration of distribution and integration of the devices is not limited to that shown in the drawings. All or some devices can be configured such that the devices are functionally or physically distributed and integrated in arbitrary units depending on various additions or functional load. For example, all or some processing functions of the devices in the RNA identification apparatus 100, the client apparatus 200 or the server apparatus 400, in particular, processing functions performed by the control section may be realized by a central processing unit (CPU) and a program interpreted and executed by the CPU or may also be realized by hardware realized by a wired logic. The program is recorded on a recording medium (will be described later) and mechanically read by the devices as needed. More specifically, on the storage unit such as a ROM or an HD, a computer program which gives an instruction to the CPU in cooperation with an operating system (OS) to perform various processes is recorded. The computer program is executed by being loaded on a RAM, and constitutes a control section in cooperation with the CPU.

The computer program may be stored in an application program server connected to each of the devices through an arbitrary network. The computer program in whole or in part may be downloaded as needed. A program which causes a computer to execute a method according to the present invention may also be stored in a computer readable recording medium. In this case, the "recording medium" includes an arbitrary "portable physical medium" such as a flexible disk, a magnet-optical disk, a ROM, an EPROM, an EEPROM, a CD-ROM, an MO, or a DVD or a "communication medium" such as a communication line or a carrier wave which holds a program for a short period of time when the program is transmitted through a network typified by a LAN, a WAN, and the Internet. The "program" is a data processing method described in an arbitrary language or a describing method. As a format of the "program", any format such as a source code or a binary code may be used. The "program" is not always singularly constructed, and includes a program obtained by distributing and arranging multiple modules or libraries or a program that achieves the function in cooperation with another program typified by an operating system (OS). In the apparatuses according to the embodiments, as a specific configuration to read a recording medium, a read procedure, an install procedure used after the reading, and the like, known configurations and procedures may be used.

Various databases or the like stored in the storage section are a memory device such as a RAM or a ROM, a fixed disk device such as a hard disk drive, and a storage unit such as a flexible disk or an optical disk and store various programs, tables, databases, Web page files used in various processes or Web site provision. Each of the devices may be realized by connecting a known information processing apparatus such as a personal computer or a workstation and installing software (including a program, data, or the like) which causes the information processing apparatus to realize the method according to the present invention.

The constituent elements need not be always physically arranged as shown in the drawings. Furthermore, a specific configuration of distribution and integration of the devices is not limited to that shown in the drawings. All or some devices can be configured such that the devices are functionally or physically distributed and integrated in arbitrary units depending on various additions or functional load.

INDUSTRIAL APPLICABILITY

As explained above in detail, a ribonucleic acid identification apparatus, a ribonucleic acid identification method, a program, and a ribonucleic acid identification system according to the present invention can dramatically improve identification reliability of individual digests by obtaining nucleic acid residue sequence information from not only digest molecular weights that provide only nucleic acid residue composition, but also a set of product ion masses and are extremely useful in various fields such as medical care, pharmaceutical production, drug development, biological research, and clinical tests.

EXPLANATION OF REFERENCE NUMERALS

100 APPARATUS FOR IDENTIFICATION OF RIBONUCLEIC ACID,
102 CONTROL SECTION
102a MEASURED FRAGMENT MOLECULAR WEIGHT EXTRACTION SECTION
102b FRAGMENTATION SECTION
102c THEORETICAL FRAGMENT MOLECULAR WEIGHT COMPUTATION SECTION
102e CANDIDATE THEORETICAL FRAGMENT MOLECULAR WEIGHT EXTRACTION SECTION
102f CANDIDATE FRAGMENT SEQUENCE EXTRACTION SECTION

102g THEORETICAL PRODUCT ION MASS COMPUTATION SECTION
102h MEASURED PRODUCT ION MASS EXTRACTION SECTION
102i ASSIGNMENT SCORE COMPUTATION SECTION
102j CANDIDATE SEQUENCE IDENTIFICATION SECTION
102k OCCURRENCE PROBABILITY COMPUTATION SECTION
102p ENTRY SCORING SECTION
102q ENTRY IDENTIFICATION SECTION
102n MODIFICATION CONVERSION SECTION
106 STORAGE SECTION
106a NUCLEIC ACID SEQUENCE DB
106b FRAGMENTATION RULES TABLE
106c MASS DEFINITION TABLE
106d MODIFICATION RULES TABLE
106g PEAK LIST
106e FRAGMENT SEQUENCE TABLE
106i CANDIDATE FRAGMENT SEQUENCE LIST
106j THEORETICAL PRODUCT ION TABLE
106k IDENTIFIED FRAGMENT TABLE
106m IDENTIFIED NUCLEIC ACID ENTRY TABLE TANDEM TYPE MASS ANALYZER
200 CLIENT APPARATUS
202a PEAK ACQUISITION SECTION
202p SEARCH CONDITION INPUT SECTION
202q RESULT OUTPUT SECTION
212 INPUT SECTION
214 OUTPUT SECTION
300 NETWORK
400 SERVER APPARATUS
402r RESULT TRANSMISSION SECTION
406 INTERNAL DB
500 EXTERNAL DATABASE
600 NETWORK

The invention claimed is:

1. An apparatus for identifying a ribonucleic acid, comprising a memory and a processor,
wherein the memory comprises:
a peak list that stores the peaks of a spectrum extracted from tandem mass spectrometry data of a ribonucleic acid cleaved by enzymatic cleavage;
a ribonucleic acid sequence database that stores ribonucleic acid sequences; and
a fragmentation rules table that stores fragmentation rules corresponding to the enzymatic cleavage; and
wherein the processor is configured to:
extract measured fragment molecular weights from the peaks;
fragment a candidate ribonucleic acid sequence from the ribonucleic acid sequence database into fragment sequences by referring to the fragmentation rules;
compute theoretical fragment molecular weights for the fragment sequences;
extract candidate theoretical fragment molecular weights from the theoretical fragment molecular weights that correspond to the measured fragment molecular weights by comparing the theoretical fragment molecular weights with the measured fragment molecular weights;
extract candidate fragment sequences corresponding to the candidate theoretical fragment molecular weights, from the fragment sequences;
compute the theoretical product ion masses for the candidate fragment sequences according to predetermined dissociation rules;
extract measured product ion masses from the peaks;
score the candidate fragment sequences by comparing the theoretical product ion masses with the measured product ion masses to produce scores; and
identify fragment sequences of the ribonucleic acid from the candidate fragment sequences based on the scores.

2. The apparatus according to claim 1, wherein
the processor is further configured to:
compute the occurrence probabilities for the fragment sequences of the candidate ribonucleic acid sequence;
map the scores for the candidate fragment sequences based on the occurrence probabilities; and
identify the fragment sequences of the ribonucleic acid from the candidate fragment sequences based on the map of the scores.

3. The apparatus according to claim 1, wherein
the memory further comprises:
a modification rules table that stores modification rules for modifying the ribonucleic acid, and
the processor is further configured to:
perform a conversion between a modified sequence and an unmodified sequence for the fragment sequences by referring to the modification rules.

4. A method of identifying a ribonucleic acid in a sample, comprising the following steps performed on a computer:
obtaining peaks of a spectrum extracted from tandem mass spectrometry data of a ribonucleic acid in a sample cleaved by enzymatic cleavage;
extracting measured fragment molecular weights from the peaks;
identifying a candidate ribonucleic acid sequence from a ribonucleic acid sequence database as an object of a search;
fragmenting the candidate ribonucleic acid sequence into fragment sequences by referring to fragmentation rules corresponding to the enzymatic cleavage;
computing theoretical fragment molecular weights for the fragment sequences;

comparing the theoretical fragment molecular weights with the measured fragment molecular weights;

extracting candidate theoretical fragment molecular weights from the theoretical fragment molecular weights that correspond to the measured fragment molecular weights by comparing the theoretical fragment molecular weights with the measured fragment molecular weights;

extracting candidate fragment sequences corresponding to the candidate theoretical fragment molecular weights, from the fragment sequences;

computing the theoretical product ion masses for the candidate fragment sequences according to predetermined dissociation rules;

extracting measured product ion masses from the peaks;

scoring the candidate fragment sequences by comparing the theoretical product ion masses with the measured product ion masses; and identifying the fragment sequences of the ribonucleic acid based on the scoring.

5. The method according to claim 4, further comprising:
computing the occurrence probabilities for the fragment sequences of the candidate ribonucleic acid sequence;
mapping the scores for the candidate fragment sequences based on the occurrence probabilities; and
identifying the fragment sequences of the ribonucleic acid from the candidate fragment sequences based on the scores.

6. The method according to claim 4, wherein
the computer includes:
a modification rules table that stores modification rules for modifying the candidate ribonucleic acid sequence, and
the method further comprises:
performing a conversion between a modified sequence and an unmodified sequence for each of the fragment sequences by referring to the modification rules.

7. A non-transitory computer readable medium comprising instructions to cause a computer to execute the following steps to identify a ribonucleic acid
extract measured fragment molecular weights from peaks of a spectrum extracted from tandem mass spectrometry data of a ribonucleic acid in a sample cleaved by enzymatic cleavage;
fragment a candidate ribonucleic acid sequence into fragment sequences by referring to fragmentation rules corresponding to the enzymatic cleavage;
compute theoretical fragment molecular weights for the fragment sequences;
extract candidate theoretical fragment molecular weights that correspond to measured fragment molecular weights by comparing the theoretical fragment molecular weights with the measured fragment molecular weights;
extract candidate fragment sequences corresponding to the candidate theoretical fragment molecular weights, from the fragment sequences;
compute theoretical product ion masses for the candidate fragment sequences according to predetermined dissociation rules;
extract measured product ion masses from the peaks;
score the candidate fragment sequences by comparing the theoretical product ion masses with the measured product ion masses to produce scores; and
identify the fragment sequences of the ribonucleic acid from the candidate fragment sequences based on the scores.

8. The non-transitory computer readable medium according to claim 7, further comprising instructions to cause the computer to execute the following steps:
computing the occurrence probabilities for the fragment sequences of the candidate ribonucleic acid sequence;
mapping the scores for the candidate fragment sequences based on the occurrence probabilities; and
identifying the fragment sequences of the ribonucleic acid from the candidate fragment sequences based on a map of the scores.

9. The non-transitory computer readable medium according to claim 7, wherein
the medium further includes:
a modification rules table that stores modification rules for modifying the ribonucleic acid, and
the computer readable medium further comprise instructions to cause a computer to execute the following step:
performing a conversion between a modified sequence and an unmodified sequence for each of the fragment sequences by referring to the modification rules.

10. A system for of identifying a ribonucleic acid in a sample, comprising a client apparatus and a server apparatus,
wherein the client apparatus comprises a control section, a storage section, an input section, and an output section;
wherein the server apparatus comprises a control section and a storage section;
wherein the client apparatus control section is configured to:
acquire the peaks of a spectrum extracted from tandem mass spectrometry data of a ribonucleic acid in a sample cleaved by enzymatic cleavage and store the acquired peaks in the client apparatus storage section while simultaneously transmitting the peaks to the server apparatus,
store search conditions inputted from the client apparatus input section and appoint an enzymatic cleavage method in the client apparatus storage section while simultaneously transmitting the search conditions to the server apparatus; and
output fragment sequences of the ribonucleic acid identified at the server apparatus and transmitted from the server apparatus, through the output section;
wherein the server apparatus control section is configured to:
extract measured fragment molecular weights from the peaks;
fragment a candidate ribonucleic acid sequence into fragment sequences by referring to fragmentation rules corresponding to the enzymatic cleavage;
compute theoretical fragment molecular weights for the fragment sequences;
extract candidate theoretical fragment molecular weights from the theoretical fragment molecular weights that correspond to the measured fragment molecular weights by comparing the theoretical fragment molecular weights with the measured fragment molecular weights;
extract candidate fragment sequences corresponding to the candidate theoretical fragment molecular weights from the fragment sequences;
compute theoretical product ion masses for the candidate fragment sequences according to predetermined dissociation rules;
extract measured product ion masses from the peaks;
score candidate fragment sequences by comparing the theoretical product ion masses with the measured product ion masses;

identify the fragment sequences of the ribonucleic acid from the candidate fragment sequences based on the scores; and transmit the identified fragment sequences to the client apparatus.

11. The system according to claim 10, wherein the server apparatus control section is further configured to:

compute the occurrence probabilities for the fragment sequences of the candidate ribonucleic acid sequence;

map the scores for the candidate fragment sequences based on the occurrence probabilities; and identify the fragment sequences of the ribonucleic acid from the candidate fragment sequences based on the map of the scores.

12. The system according to claim 10, wherein the storage section of the server apparatus further includes:
- a modification rules table that stores modification rules for modifying the ribonucleic acid, and the control section of the server apparatus further includes:
- a modification conversion unit that is configured to perform a conversion between a modified sequence and an unmodified sequence for the fragment sequences by referring to the modification rules.

* * * * *

SEQUENCE LISTING

<160> NUMBER OF SEQ ID NOS: 7

<210> SEQ ID NO 1
<211> LENGTH: 121
<212> TYPE: DNA
<213> ORGANISM: Saccharomyces cerevisiae

<400> SEQUENCE: 1
ggttgcggcc atatctacca gaaagcaccg ttctccgtcc gatcaactgt agttaagctg     60
gtaagagcct gaccgagtag tgtagtgggt gaccatacgc gaaactcagg tgctgcaatc    120
t                                                                   121

<210> SEQ ID NO 2
<211> LENGTH: 121
<212> TYPE: DNA
<213> ORGANISM: Saccharomyces cerevisiae

<400> SEQUENCE: 2
ggttgcggcc atatctacca gaaagcaccg tttcccgtcc gatcaactgt agttaagctg     60
gtaagagcct gaccgagtag tgtagtgggt gaccatacgc gaaactcagg tgctgcaatc    120
t                                                                   121

<210> SEQ ID NO 3
<211> LENGTH: 121
<212> TYPE: DNA
<213> ORGANISM: Saccharomyces cerevisiae

<400> SEQUENCE: 3
ggttgcggcc atatctacca gaaagcaccg tttcccgtcc gatcaactgt agttaagctg     60
gtaagagcct gaccgagtag tgtagtgggt gaccatacgc gaaactcagg tgctgcaatc    120
t                                                                   121

<210> SEQ ID NO 4
<211> LENGTH: 117
<212> TYPE: DNA
<213> ORGANISM: Saccharomyces cerevisiae

<400> SEQUENCE: 4
ggttgcggcc atatctacca gaaagcaccg tttcccgtcc gatcaactgt agttaagctg     60
gtaagagcct gaccgagtag tgtagtgggt gaccatacgc gaaactcagg tgctgca       117

```
<210> SEQ ID NO 5
<211> LENGTH: 117
<212> TYPE: DNA
<213> ORGANISM: Saccharomyces cerevisiae

<400> SEQUENCE: 5
ggttgcggcc atatctacca gaaagcaccg tttcccgtcc gatcaactgt agttaagctg      60
gtaagagcct gaccgagtag tgtagtgggt gaccatacgc gaaactcagg tgctgca       117

<210> SEQ ID NO 6
<211> LENGTH: 117
<212> TYPE: DNA
<213> ORGANISM: Saccharomyces cerevisiae

<400> SEQUENCE: 6
ggttgcggcc atatctacca gaaagcaccg tttcccgtcc gatcaactgt agttaagctg      60
gtaagagcct gaccgagtag tgtagtgggt gaccatacgc gaaactcagg tgctgca       117

<210> SEQ ID NO 7
<211> LENGTH: 117
<212> TYPE: DNA
<213> ORGANISM: Saccharomyces cerevisiae

<400> SEQUENCE: 7
ggttgcggcc atatctacca gaaagcaccg tttcccgtcc gatcaactgt agttaagctg      60
gtaagagcct gaccgagtag tgtagtgggt gaccatacgc gaaactcagg tgctgca       117
```